(12) United States Patent
Diefenbach et al.

(10) Patent No.: US 12,005,317 B2
(45) Date of Patent: Jun. 11, 2024

(54) PATIENT DATA VISUALIZATION, CONFIGURATION OF THERAPY PARAMETERS FROM A REMOTE DEVICE, AND DYNAMIC CONSTRAINTS

(71) Applicants: Drexel University, Philadelphia, PA (US); Paul J. Diefenbach, Collingswood, NJ (US); Robert C. Gray, Seattle, WA (US); Timothy J. Day, Philadelphia, PA (US); Margaret E. O'Neil, Philadelphia, PA (US)

(72) Inventors: Paul J. Diefenbach, Collingswood, NJ (US); Robert C. Gray, Seattle, WA (US); Timothy J. Day, Philadelphia, PA (US); Margaret E. O'Neil, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 16/481,481

(22) PCT Filed: Feb. 12, 2018

(86) PCT No.: PCT/US2018/017854
§ 371 (c)(1),
(2) Date: Jul. 28, 2019

(87) PCT Pub. No.: WO2018/148674
PCT Pub. Date: Aug. 16, 2018

(65) Prior Publication Data
US 2019/0371114 A1 Dec. 5, 2019

Related U.S. Application Data

(60) Provisional application No. 62/489,649, filed on Apr. 25, 2017, provisional application No. 62/457,419, filed on Feb. 10, 2017.

(51) Int. Cl.
*A61B 5/00* (2006.01)
*A61B 5/11* (2006.01)
*A63B 24/00* (2006.01)

(52) U.S. Cl.
CPC ........ *A63B 24/0075* (2013.01); *A61B 5/0022* (2013.01); *A61B 5/1121* (2013.01);
(Continued)

(58) Field of Classification Search
CPC . A63B 24/0075; A61B 5/0022; A61B 5/1121; A61B 5/1128; A61B 2505/09; A61B 2024/0096
See application file for complete search history.

(56) References Cited

U.S. PATENT DOCUMENTS 6,712,692 B2 3/2004 Basson et al.
7,602,301 B1 10/2009 Stirling et al.
(Continued)

FOREIGN PATENT DOCUMENTS

WO 2018/148674 A1 8/2018

OTHER PUBLICATIONS

International Search Report and Written Opinion received for PCT Application No. PCT/US2018/017854, dated Apr. 27, 2018, 6 pages.
(Continued)

*Primary Examiner* — Corbett B Coburn
(74) *Attorney, Agent, or Firm* — Schott, P.C.

(57) ABSTRACT

A system for delivering physical therapy to a user includes an active video gaming system that has a motion detector capable of detecting the physical motions of a user. The system includes parameters related to movement restrictions that a user may have and the system creates a gaming environment based on the parameters.

19 Claims, 13 Drawing Sheets

(52) U.S. Cl.
CPC ......... *A61B 5/1128* (2013.01); *A61B 2505/09* (2013.01); *A63B 2024/0096* (2013.01)

(56) References Cited

U.S. PATENT DOCUMENTS

| | | | |
|---|---|---|---|
| 7,967,728 | B2 | 6/2011 | Zavadsky et al. |
| 9,161,708 | B2 | 10/2015 | Elliott et al. |
| 2009/0083070 | A1 | 3/2009 | Giftakis et al. |
| 2011/0275042 | A1 | 11/2011 | Warman et al. |
| 2012/0165098 | A1 | 6/2012 | Raptis et al. |
| 2013/0123667 | A1 | 5/2013 | Komatireddy et al. |
| 2014/0031098 | A1* | 1/2014 | Tacconi ............. A63B 71/0009 463/7 |
| 2014/0194250 | A1 | 7/2014 | Reich et al. |
| 2014/0322686 | A1 | 10/2014 | Kang |
| 2015/0148113 | A1 | 5/2015 | Klein et al. |
| 2016/0096073 | A1 | 4/2016 | Rahman et al. |
| 2016/0129335 | A1 | 5/2016 | Domansky et al. |
| 2016/0256771 | A1* | 9/2016 | Ekbia ..................... G06Q 50/22 |
| 2017/0000388 | A1* | 1/2017 | Jessen ..................... A61B 5/112 |

OTHER PUBLICATIONS

Taylor et al., "Activity-promoting gaming systems in exercise and rehabilitation", Journal of Rehabilitation Research & Development, vol. 48, Issue No. 10, Oct. 2011, 26 pages.

Freitas et al., "Development and Evaluation of a Kinect Based Motor Rehabilitation Game", SBC—Proceedings of SBGames 2012, Nov. 2-4, 2012, pp. 144-153.

Gray, Robed C., "Adaptive Game Input Using Knowledge of Player Capability: Designing for Individuals with Different Abilities", Master of Science in Digital Media, Drexel University, Jan. 2018, pp. 1-88.

* cited by examiner

KOLLECT

OVERRIDE SETTINGS FOR KOLLECT

| SPLATS | FALSE |
| HAZARDS | 11 |
| THEME | SHAPES |
| | GEMS |
| UPDA | SPORTS |
| | SPACE |
| | FRUIT |
| | SPOOKY |
| | PATS |
| | FANATASY |
| | VEHICLES |
| | COWBOY |

DEFAULT SETTINGS FOR KOLLECT

GRAPHICS:

| BACKGROUND | SHAPES |
| KOLLECT | SHAPES |

RULES:

| GAME LENGTH | 2 |
| WAVE TIME | 8 |
| REST TIME | 2 |
| BONUS TIME | 4 |
| BONUS ROUND | TRUE |
| WAVE FAIL | 1 |
| WAVE WIN | 0.5 |

DIFFICULTY:

| HAZARD SCALE | 1 |
| OBJECT SCALE | 1 |
| OBJECTS | 4 |
| ATTRACT RADIUS | 3 |

*FIG. 2*

NODE METRIC + INPUT RESOLUTION SCHEMA COMPATIBILITY

|  | POSITION | ORIENTATION | VECTOR BETWEEN | ANGLE BETWEEN |
|---|---|---|---|---|
| TRIGGER | ✓ | ✓ | ✓ | ✓ |
| SIGNAL | ✓ | ✓ | ✓ | ✓ |
| RANGE | ✓ | ✓ | ✓ | ✓ |
| LOCATION2D | ✓ | ✓ | ✓ | ✗ |
| LOCATION3D | ✓ | ✓ | ✓ | ✗ |

✓ SCHEMA IS POSSIBLE
✗ SCHEMA IS NOT POSSIBLE

FIG. 12

NODE METRIC + INPUT RESOLUTION OPERATOR COMPATIBILITY

|  | POSITION | | | | ORIENTATION | | | | VECTOR BETWEEN | | | | ANGLE BETWEEN | | | |
|---|---|---|---|---|---|---|---|---|---|---|---|---|---|---|---|---|
|  | % | ▽ | ? | ‖ | % | ▽ | ? | ‖ | % | ▽ | ? | ‖ | % | ▽ | ? | ‖ |
| TRIGGER | ✹ | ✓ | ✓ | ✗ | ✹ | ✓ | ✓ | ✗ | ✹ | ✓ | ✓ | ✗ | ✗ | ✗ | ✓ | ✗ |
| SIGNAL | ✹ | ✓ | ✓ | ✗ | ✹ | ✓ | ✓ | ✗ | ✹ | ✓ | ✓ | ✗ | ✗ | ✗ | ✓ | ✗ |
| RANGE | ✹ | ✓ | ✗ | ✓ | ✹ | ✓ | ✗ | ✓ | ✹ | ✓ | ✗ | ✓ | ✗ | ✗ | ✗ | ✓ |
| LOCATION2D | ✹ | ✗ | ✗ | ✓ | ✹ | ✗ | ✗ | ✓ | ✹ | ✗ | ✗ | ✓ | ✗ | ✗ | ✗ | ✓ |
| LOCATION3D | ✹ | ✗ | ✗ | ✓ | ✹ | ✗ | ✗ | ✓ | ✹ | ✗ | ✗ | ✓ | ✗ | ✗ | ✗ | ✓ |

COMPONENT TYPE:
  % CALCULATION - CONVERTS A VECTOR INTO ANOTHER VECTOR
  ▽ REDUCTION - REDUCES A VECTOR TO A SCALAR
  ? CONDITIONAL - EVALUATES A SCALAR TO PRODUCE A BOOLEAN
  ‖ BOUNDS - NORMALIZES A VECTOR OR SCALAR TO THE SAME TYPE

COMPONENT TYPE:
  ✓ -SCHEMA MUST HAVE THIS OPERATOR
  ✗ -SCHEMA CANNOT HAVE THIS OPERATOR
  ✹ -SCHEMA CAN (BUT DOES NOT HAVE TO) HAVE THIS OPERATOR

FIG. 13

| | |
|---|---|
| NAME | A STRING THAT WILL UNIQUELY IDENTIFY THIS SCHEMA AT RUNTIME. |
| RESOLUTION | THE TYPE OF INPUT RESOLUTION TO WHICH THIS NAMED SCHEMA IS TIED. "TRIGGER" - A SINGLE TIMED EVENT. "SIGNAL" - A BOOLEAN INDICATING WHETHER A STATE IS ACTIVE. "RANGE" - A FLOATING POINT VALUE BETWEEN 0 AND 1. "LOCATION2D" - A 2D VECTOR (X, Y). "LOCATION3D" - A 3D VECTOR (X, Y, Z). |
| DEVICE | THE TYPE OF KINEMATIC SENSOR. "KINECT" - THE MICROSOFT KINECT V2 SENSOR. "LEAP" - THE LEAP MOTION CONTROLLER SENSOR. |
| METRIC | THE METRIC FROM THE KINEMATIC DEVICE NODE(S) TO EVALUATE. "POSITION" - THE LOCATION OF A NODE IN A 3D SPACE(VECTOR). "ORIENTATION" - THE ORIENTATION OF A NODE (VECTOR). "VECTORBETWEEN" - THE VECTOR BETWEEN TWO NODES (VECTOR). "ANGLEBETWEEN" - THE ANGLE FORMED IN THE NODE TRIAD (SCALAR) |
| NODES | ONE OR MORE BODY NODES DEFINED BY THE DEVICE (E.G. "HEAD"). |
| CALCULATION | PERFORMS A VECTOR CALCULATION ON THE INITIAL METRIC. "CROSSPRODUCT" - CROSS PRODUCT AGAINST AN OPERAND VECTOR. "ADD" - ADD TO AN OPPERAND VECTOR. "MULTIPLY" - SCALE BY AN OPERAND VECTOR |
| REDUCTION | REDUCES A VECTOR VALUE TO A SCALAR. "DOT PRODUCT" - DOT PRODUCT AGAINST AN OPERAND VECTOR. "X/Y/ZVALUE" - EXTRACT THE VECTOR COMPONENT. |
| CONDITION | IF RESOLUTION IS A TRIGGER/SIGNAL, DEFINES THE VALUE THRESHOLD. "GREATERTHAN/EQUAL/LESSTHAN" - COMPARE VALUE TO SCALAR. |
| BOUNDS | IF RESOLUTOIN IS A RANGE/LOCATION, DEFINES THE NORMALIZTION. |

FIG. 14

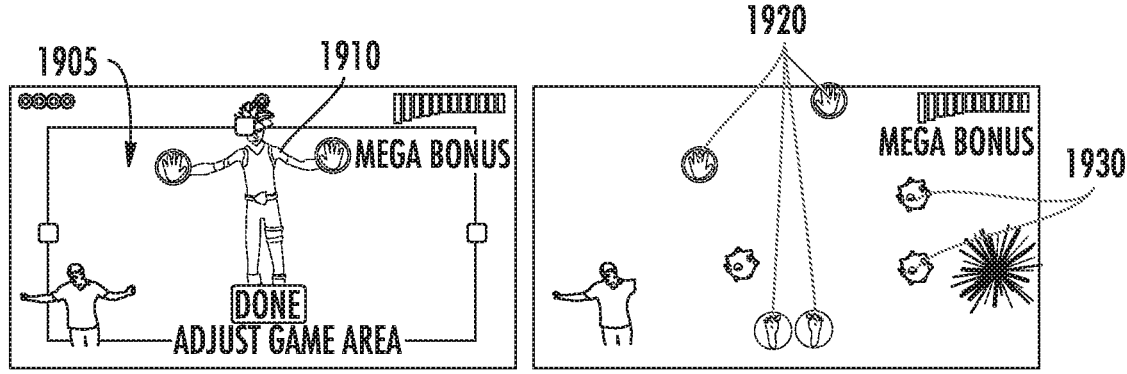
FIG. 19A                    FIG. 19B

PATENT DATA VISUALIZATION, CONFIGURATION OF THERAPY PARAMETERS FROM A REMOTE DEVICE, AND DYNAMIC CONSTRAINTS

BACKGROUND

Physical therapy sessions typically involve a clinician working together with a patient through a prescribed course of exercises. In these cases, it is easy for the clinician to alter the therapy mid-session to changing demands, such as decreasing intensity or adding challenge as they observe the patient's response to the therapy. An emerging technology is known as Active Video Games (AVG) and may be used as a therapy tool for patients with neuromuscular disabilities. Though the use of software provides many potential benefits to therapeutic treatment, one disadvantage is that pre-built software no longer carries the same flexibility as therapy that is manually applied.

Further, in traditional neuromuscular therapy administration and research, videos of patient movement captured during clinical sessions can be analyzed to provide insight into the details of a patient's disability. A trained clinician can analyze the video following a session to understand the limitations of mobility and suggest therapeutic intervention that can help the patient improve their mobility. This video data is also of interest to researchers in the field, who perform similar analysis to gain insight and improve the state of the art.

The use of captured video in both of these situations can be limiting or burdensome to the process of analyzing patient movement. Since the video contains data that uniquely identifies the patient, it is considered to be Protected Health Information (PHI) and requires additional process and protection. Video data also requires relatively large digital files, making storage and communication of the data inconvenient.

Another aspect of therapy is that neuromuscular disabilities do not affect every patient in the same way, and therapeutic needs vary from person-to-person. For example, some patients may have varying mobility across limbs, or may prefer a seated position or require a wheelchair. For these players, determining an appropriate expectation of mobility within the game offers the specificity required to target a single body part or injured area, avoid areas that shouldn't be activated, and provide more directed therapy.

Looking at typical AVG software, it presumes normal human movement capability in their players, and game design platforms do not place any constraint or provide to the developers a mechanism for managing alternative capabilities.

Thus, one particular complication in the development of AVGs for therapy is the increased complexity of writing input routines based on human body motion, which provides a much larger and more complex domain than traditional, discrete-input game controllers. And another complication lies in individualizing a therapy game experience to an individual player because developers must program software with static routines that cannot be modified once compiled and released.

SUMMARY OF THE EMBODIMENTS

A system for delivering physical therapy to a user includes an active video gaming system comprising a motion detector capable of detecting the physical motions of a user; setting parameters related to movement restrictions that a user may have; creating a gaming environment based on the parameters.

A System for Unified Kinematic Input (SUKI) is a software library that addresses some of the above issues as well. SUKI enables games to adapt to players' specific therapeutic goals by mapping arbitrary human body movement input to game mechanics at runtime, allowing user-defined body motions to drive gameplay without requiring any change to the software. Additionally, the SUKI library may implement a dynamic profile system that alters the game's configuration based on known physical capabilities of the player and updates this profile based on the player's demonstrated ability during play.

BRIEF DESCRIPTION OF THE DRAWINGS

FIG. 2 shows a subset of parameters that may be set.

FIG. 12 displays the Node Metric and Input Resolutions that may be combined to form a valid schema.

FIG. 13 displays the Node Metric and Input Resolution Operator compatibility.

FIG. 14 shows SUKI schema JSON fields.

FIGS. 19A and 19B show a game configuration and implementation screen.

DETAILED DESCRIPTION OF THE EMBODIMENTS

1. Introduction

Using AVG systems combined with a medical professional's knowledge of a patient's needs, the current system changes the way in which clinicians deliver and patients receive therapy, and, in particular, physical therapy. The system may also be used in wellness programs to maintain fitness and in rehabilitation for joint replacement and other medical procedures and other health and wellness activities that include exercise movements.

2. Remote Configuration and Dosing

The system provides therapists and clinicians with the ability to define therapeutic goals before a session as well as modify those parameters during the course of a session, altering the program in real time and affecting prescribed therapy to the patient on demand. This may enable AVG-based therapy to receive the benefits of a software-based solution while still maintaining parity with traditional therapy methods in terms of usability and effectiveness.

The technology that supports this flexibility may be implemented in the form of a programming mechanism exposed to developers via a platform library and integrates with other systems developed for that library (see SUKI discussion below). Additionally, a programming paradigm around this mechanism may assist game designers in developing games that achieve this flexibility.

Further, intelligent systems may automatically apply changes to parameters during a session ("auto-dosing") based on higher-level guidance set by the care provider. This may enable users to receive effective therapy even in the absence of their care provider (e.g., sessions at home).

Care providers (or an automated process) may prescribe and adjust the therapy experience in a video game both during and between games, implemented as and assisted by a programming mechanism and paradigm that enable game developers to manage and actualize those changes within the game at runtime.

This dosing and configuration differs from calibration because dosing focuses on presenting a desired challenge to the player/patient, rather than considering the player's limitations.

Figure 1:
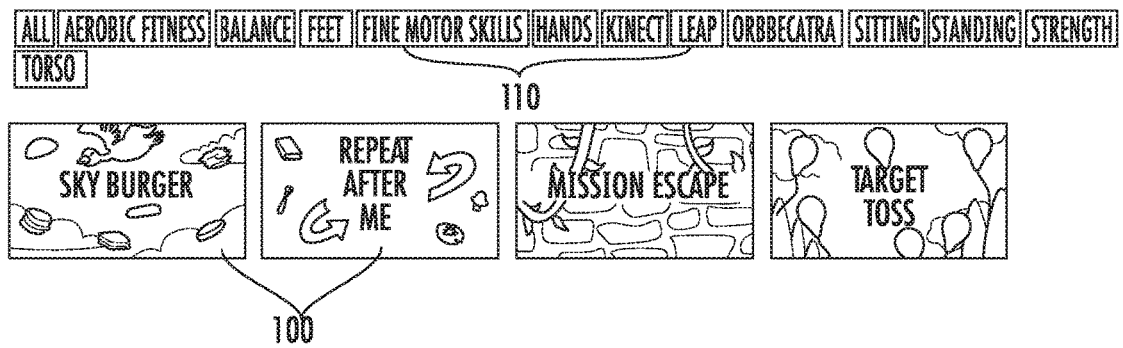
FIG. 1 shows a screen shot of potential games offered within the system.

The remote configuration and dosing methods include therapist tools for adjusting the therapeutic experience for patients by: (1) changing the availability of games in the system (FIG. 1 shows some of the available games 100, sortable by certain categories or therapeutic tags 110 like torso mobility, hip flexion, etc.), (2) using special tools to define dosing parameters, (3) adjusting game parameters for the player's sessions ahead of time (FIG. 2 shows some of the parameters relating to certain in-game hazards and objects that increase or decrease the game difficulty), and (4) manipulating aspects of gameplay in real time during a patient's session.

Medical professional may limit the games available to a patient, based on the therapeutic tags 110 or the professional may provide game availability based on player participation in either a time-based or achievement-based manner.

Figure 3:
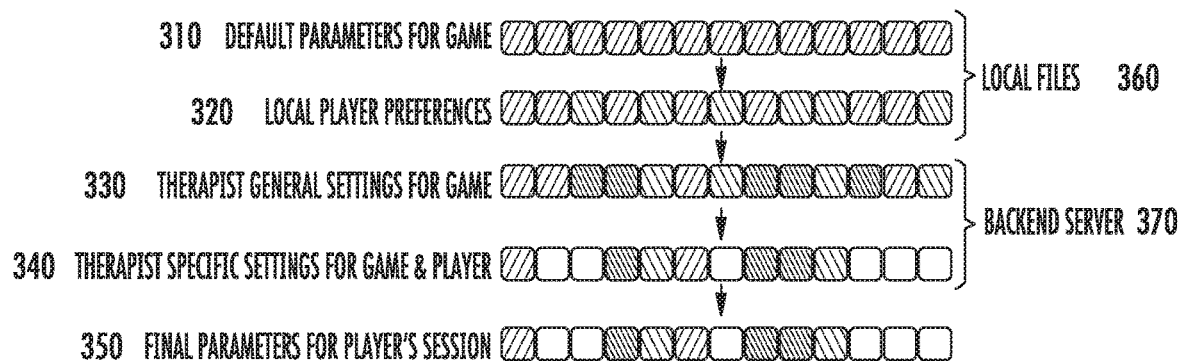
FIG. 3 shows a hierarchical relationship between the parameters.

Parameters may be structured and defined in different ways. For example, parameters may be organized into a hierarchy of parameters—cascading relationships among sources such as that shown in FIG. 3, which shows a relationship hierarchy between different system users and their parameter settings, where each block represents a different parameter. In the example shown in FIG. 3, the game may have a specific set of default parameters 310, player preferences 320, therapist general settings for a game 330, therapist specific settings 340, and final parameters for a session 350. Each one of the hierarchies may override the one before it. As shown, the default and local parameters 310, 320 may be stored on a local server 360 and the therapist settings on a remote server 370, which allows for the remote dosing.

The system may also define parameters in terms of equations, logic, and/or programming. Further, aggregate parameter modification may allow a user to change several parameters by just updating one base dependency parameter.

For games where it is possible, users and the system may set global parameters for a patient that apply to all games. For example, a user may want a patient to focus on a patient's lower left leg movement and set a parameter to emphasize that movement. When the patient selects any one of several games, the lower left leg movement parameter may be the focus of the game, or be emphasized to ensure the patient must respond appropriately in the game.

The system may also set parameters based on specific physical, cognitive, and sensory limitations of players.

The system may define trigger parameters for dosage changes such as game stages (i.e., warmup, exercise, cooldown), based on time (after 10 minutes, switch from left to right-side emphasis), achievements (after 100 tasks accomplished, change parameter), and variable parameter interpolation.

Users and the system may allow for real-time parameter adjustment locally or remotely using hotkeys, mobile devices, or connected devices. The system may record these parameters and their changes (the parameter and the time of the change).

This remote connection may also allow others to participate with the patient (e.g., friends, family). In use, here are a few remote-dosing examples:

1.a—Therapists can determine the availability of games to a player by granting specific tags such as "cardio" or "balance" that are determined by the platform to apply to each game.

1.b—Therapists can restrict patients from playing a particular game until they achieve a certain level of mastery or accomplishment in other games first.

2.a—Parameters can be set by default, by the therapist globally, by the patient themselves, or by the therapist for a specific patient. There may be a cascading hierarchy as discussed above.

2.b—Defining some parameters in terms of their relationship to other parameters, or with conditional logic and the ability to set thresholds. For example, one parameter could be 40% of maximum heart rate. Another could be "5 objects if heart rate>=40% of maximum, else 7 objects." This allows for adaptive game play to achieve desired results.

2.c—Foundational or meta-parameters. A game designer may create a parameter called "difficulty" that serves as a base parameter from which many others are derived. For example, number of hazards, wave time, and object movement factor may be calculated off the difficulty parameter value (such as "2*difficulty"). By simply changing the single value, the therapist can affect many. This also allows game designers to create "master parameters" that define a series of sub-parameters. For example, a therapist could set a challenge level between 1-10 without needing to understand the gameplay to a substantial degree, where such detail is abstracted by the game developers.

3.a—The underlying parameter triggers may be created via the interface developed in 2.b. For example, changing wave speed depending on how much time has passed. When the heart rate hits 40%, the parameters change to x. When they collect 50 objects, the parameters change to x. The ability to define transitions between changing parameters—for example, at time 17:30 I want x parameters, at 20:00 I want y. I don't want that to happen instantly, but perhaps via a curve or linear interpolation. The ability to define the curve (step, slerp, etc.).

4.a—Player (or in-person Therapist) can adjust parameters by pressing pre-defined keys on the keyboard during gameplay. For example, they could change between different calibration windows to test different arms at different points in the session.

4.b—Adjustment of parameters during gameplay from a "second screen" such as a mobile device that is attached to the running game via a network connection.

4.d—Multiplayer therapy in which a second person (e.g. parent or therapist) can participate in the gameplay alongside the player from a second device—adding challenges or manipulating gameplay elements to join in on the therapy experience.

3. Data Visualization

Using motion-based input devices, such as the MICROSOFT KINECT, ORBBEC, ASTRA PRO, etc. Astra Pro, the system software platform may improve methods of physical therapy for patients with neuromuscular disorders. These motion-based input devices have the ability to collect detailed data regarding subject movement, including location, direction, and speed of individual body parts over time. This information ("kinematic data") may be presented in a raw numerical format, where it is typically interpreted by software to determine player intent within an application (e.g., motion-based video game).

Figure 4:
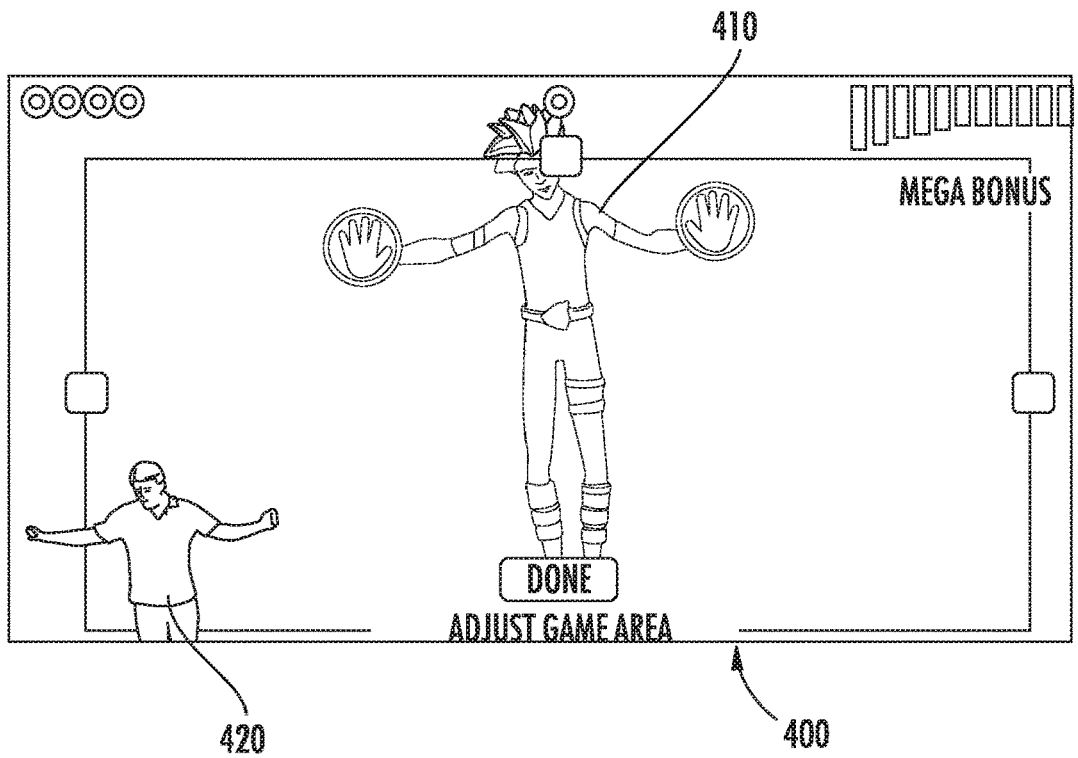
FIG. 4 shows an avatar representation of the user.

However, video data remains an important tool in traditional therapy and research analysis, and raw kinematic data alone may not provide the visibility that suits current methods of analysis. The system thus may convert raw data into a reconstructed "virtual" video replay of the movement using an avatar that meets the needs of researchers studying the data. In appearance, this may be the same or different from the calibration screen 400 shown in FIG. 4. In the calibration screen in FIG. 4, an avatar 410 is shown. For the sake of explanation, the figure also shows the player/patient 420. In use, the calibration may or may not include the player/patient overlay 420 but for the purposes of FIG. 4, the calibration screen is meant to show that the movement of the player/patient 420 with arms outstretched corresponds to the avatar 410.

Thus, during calibration, the system may prompt a player/patient to "Outstretch your arms" with an appropriate model of the movement. Players will perform the movement to the best of their ability, and establish a baseline calibration for the movement in the system.

Figure 21:
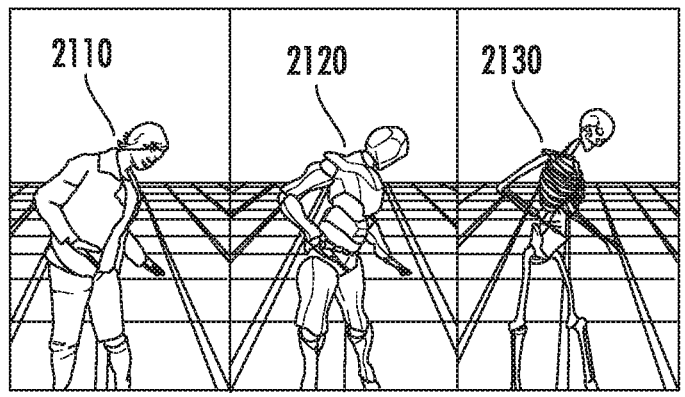
FIG. 21 shows how the system may generate a video replay of patient movement from kinemati data using an abstracted human model as an avatar for the patient.

During and after gameplay, the system may generate a video replay of patient movement from kinematic data using an abstracted human model as an avatar as shown in FIG. 21 for the patient, and use this video as way to substitute blinded data for traditional videos containing PHI to improve therapeutic research. Medical professionals may visualize the kinematic data following patient rehabilitation sessions. This provides a patient privacy as to identify and allows for the medical professional to study the patient movement without pre-conceived bias. As shown, the visualization may include the actual avatar 2110, a joined and skinned avatar 2120, or a skeletal avatar 2120. Combinations and variations of these are also possible.

Figure 5:
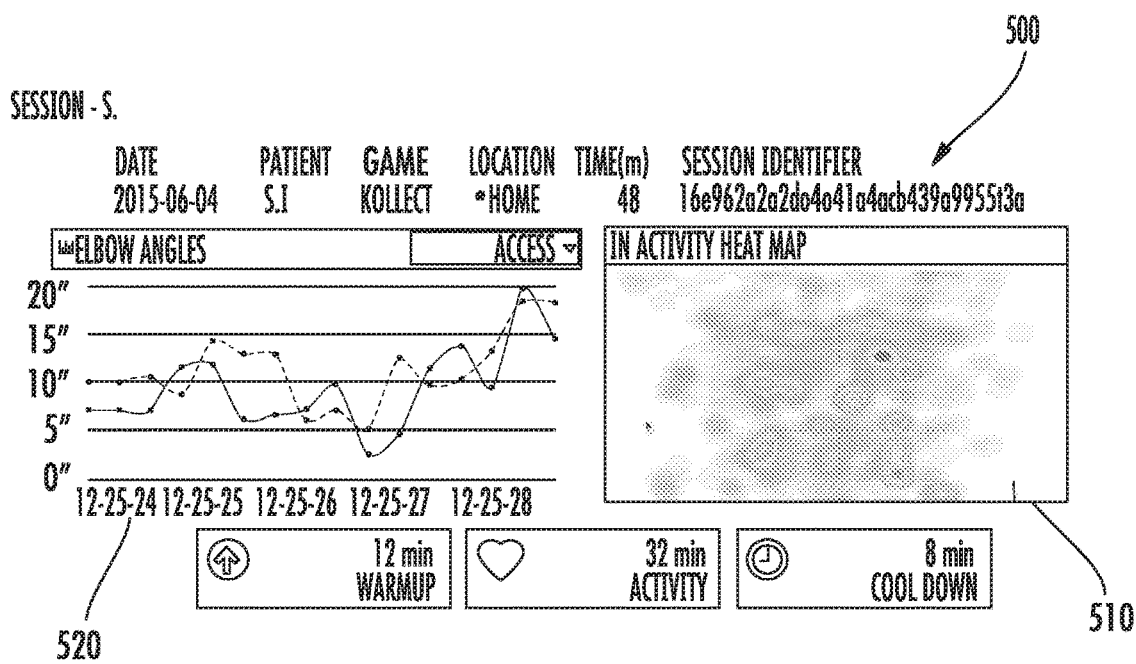
FIG. 5 shows data reported on a user's gameplay session.

These visualizations may be shown in a patient visualization screen 500 as shown in FIG. 5 and may include:

(1) useful visual analysis tools like the heat map 510 showing patient movement, (2) UI innovations for interacting with those analysis tools, (3) appropriation of the kinematic playback visuals as de-identified biomechanical data for use in research, and (4) projection of hypothetical kinematic data for reference alongside patient visualization.

The visualization of kinematic data may include 2D (FIG. 5) and 3D heat maps 510, indicating positions of key joints in space over time 520, 2D and 3D motion map, with numbers or changing colors to indicate time.

The visualizations may also include UI innovations for interacting with kinematic visualizations that include annotated timeline with game events, biometric and anthropometric data, etc., overlays of multiple visualizations (avatar+ heat map), angle marker annotations (in 3D space), hierarchical visualization—ability to dig deeper into body areas, isolate joints, view relative or global positions and orientations, VCR-type controls for pausing and speeding up (rewind, etc.) the playback, and/or rotating and zooming the view of avatar playback.

The system may allow for avatar playback videos toward creating de-identified data for biomechanical research.

The system may also use reference mannequins/ghosts to indicate multiple positions and target positions/motions.

Some examples of the system in use may include:

1.a—A 2D or 3D visualization of a cloud in which the color of the cloud at a particular location matches the time a specific body part spent at that location during the session. Similar to how a heat map might show density of population in a 2D space, etc.

2.a—A timeline shown during avatar playback that contains additional metadata regarding the session, such as game events, achievements, heart rate, and so on.

2.b—The combination of multiple visualizations to provide deeper insight. For example, a 3D heat map through which an avatar playback is shown.

2.c—Augmented reality style floating annotations overlay on the avatar playback that show numerical details for specific joints, positions, angles, etc.

2.d—Ability to switch between displaying joint orientations and positions in world coordinates vs. relative coordinates (or hierarchical rotations from shoulder→elbow→wrist).

2.e—Ability to pause, reverse, fast-forward, and so on, while also rotating and zooming on the avatar.

3—Creating and distributing avatar playbacks as a way to serve HIPAA requirements for de-identification of databases used in research.

4—showing a "ghost" avatar to provide comparison to what proper movement would look like, what previous performance looked like, or how other partner patients or friends perform.

4. Calibration of Game

AVG gameplay may need calibration to individual movement. And knowledge of mobility constraints within an application may enable developers to set proper gameplay expectations for the player, such as avoiding objectives that would require excluded motion. Further, the ability for this mechanism to adapt or change from player-to-player, or even during gameplay for a single player, may be valuable toward therapeutic goals.

The system may thus calibrate appropriate mobility expectations for individual patients in view of therapeutic goals. This process may provide not only manual adjustment, but also automatic assessment based on a brief training session in which patient capabilities are analyzed and appropriate mobility expectation parameters are determined by system software.

Parameters regarding patient mobility expectations may be exposed via a software platform and available to developers via a platform library. Programs built with this library may refer to mobility expectation parameters and detect changes in those parameters during play to allow for adjustments at runtime.

A process by which care providers and patients can define appropriate expectations for mobility in an AVG and provide a programming mechanism and paradigm to game developers by which they can access and detect changes to those parameters at runtime.

Methods for provisioning the game environment may include expectations of player capability, which may include a way to define a collection of "things the player can/cannot do" (calibration elements) that allow for individualization of the game that can better target the unique requirements of patients.

There may be two parts to this—the first is the use of these calibration elements as a structure within the gameplay and the game programming. The second may be a collection of ideas for UI that would ease the process of defining and specifying calibration elements.

There may be user requirements/restrictions as a structure within the game's design and performance and include:

1) Body Limitations meaning that the system may take into account certain motion or physical limitations within a patient such that the game will not force a patient outside those limitations.

2) Body node extents and joint angle extents define patient joints and angle limits.

3) Compound extents (bend of elbow+rotation of shoulder).

4) Patient's unavailable gestures (making a fist, jumping).

5) Game engine support for constraints in gameplay may include game modules that interpret that calibration for the developer.

6) Language for describing the particular constraints for a patient—patient movement constraint profile.

Figure 6:
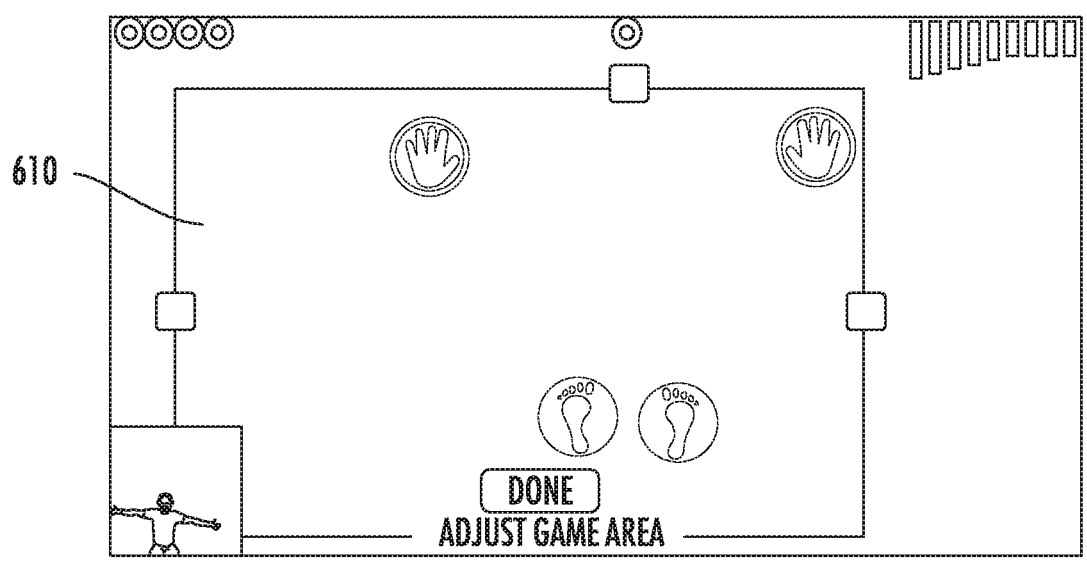
FIG. 6 shows a calibration screen

7) Gameplay-based assistance on objectives (automatic adjustment of game parameters) such that a player-patient may place more objects within reach if a player is struggling to reach them or place more objects in a sector that a player is ignoring. FIG. 6 shows hands associated with a player's movement reaching for objects.

8) Changing calibration values based on location, kinematic data, biometrics, time, achievements, etc.

9) The system may target a multitude of therapeutic goals using the same game. Thus, it adjusts the gameplay around a therapeutic goal based on the expected player capabilities in a specific therapy exercise, but also the ability to specify a different bodily movement, so that the same game can provide therapy to patients who may have completely different rehabilitation requirements. Creating a game system that would allow developers to build in such diversity easily (programming against an abstracted concept of input) means that a single game can be "calibrated" to all types of therapy goals. See Example 4 below.

The system may also include methods for describing/defining these requirements and restrictions:

1) Automatic assessment of player movement constraint profile (AI-assisted constraint determination).

Figure 7:
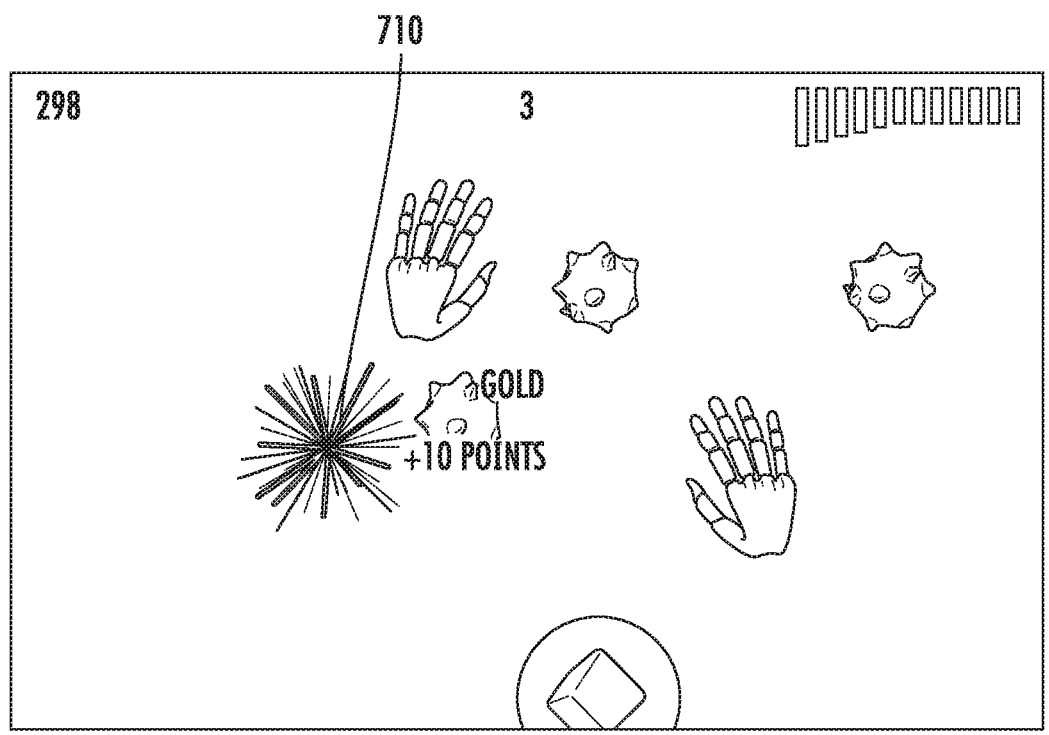
FIG. 7 shows the gaming system in use.

2) Screen-space calibration, such as by setting player reach boundaries as shown by the square in FIG. 7.

3) 3D path calibration ("capture volume"), such that a patient's movement may be tracked not just in 2D but 3D 4) Painting (e.g. heat map)

5) Defining parameters via grid structure (such as locations of objects/required movements in an area of the screen), sliders, etc.

6) Kinematic "snapshot" (move to a position to define that position)

Some examples of calibration of an AVG include:

1.a—Therapist or Player may provide the system with the angle extremes within which the patient can extend their elbow. The gameplay may work within that interval and not create gameplay objectives that would require movement beyond those extremes. Additionally, a player may indicate to the system that they are unable to make a fist with their right hand, which would automatically adjust gameplay to never require such a gesture. A therapist may also provide percentages based on a patient's personal Range of Motion (ROM), such as 80% of the maximum extent for left elbow flexion.

1.b—Game Developer may not need to write special code to track the player's elbow movement limitations. They can simply reference variables provided by the development library and build their game around them.

1.d—If the game finds that the player is having difficulty reaching objects far to the left of the screen, the gameplay may assist the player by moving the calibration extent inward over time until the player's performance improves.

1.e—Therapist or Player sets changing calibration values based on gameplay parameters or player performance. For example, player is expected to extend their left arm no further than one meter to the left. However, if target heart rate is not reached within 5 minutes of play, that calibration extends to two meters to require additional player movement.

2.a—Game instructs the player to move around for a time, during which it determines player movement limitations from kinematic data automatically. Similarly, a player could be asked to stretch as far as they could in multiple directions, which the software would use to assess limits.

2.b—As shown in FIG. 6, the therapist or player draws or designates a square 610 on the screen to serve as the bounds within which gameplay will take place. For example, before the game begins, the player draws a square on the right half of the screen. In the game (FIG. 7), objects 710 to be interacted with may only appear within the bounds of that square, which require use of the player's right arm (and not the left).

2.d—Therapist or Player designates the desired concentration of gameplay objectives throughout a 2D or 3D space by moving their hands through space or a stylus or mouse on screen throughout that space, painting it with a heat map. The values of the heat map, derived from the amount of time the stylus or hands spent in that area or the color or intensity of marking used in that area, reflects the desired relative concentration of objectives at that location during gameplay.

2.e—Therapist or Player uses a grid system to designate locations within a 2D or 3D space and define their desired concentration of gameplay objectives.

2.f—Players indicate their limitations by moving their body and letting the kinematic sensor "snapshot" that location. For instance, guided by the system, a player sets their balance extremes first by leaning to the left and holding that position until directed to lean to the right and hold position there as well. The software calculates the extremes from these kinematic snapshots.

3.a—Setting player parameters that will apply to all games to account for deviation from average player capabilities such as motion speed, cognitive level, sensory, patient characteristic like left hemiplegia, etc. Being able to set "inverted y-axis for all games" without needing to change each game separately.

3.b—All games may have explosions and loud sounds disabled for a particular user who is sensitive to such noise. Color-blindness, controller preference, accessibility, etc.

4. Therapist prepares a session for patient Alice, who is receiving rehabilitation therapy for injury to her right arm. When the game loads, the therapist can specify the right arm as the input focus, with elbow angle as the key metric, along with how different angle positions should be interpreted by the system. Meanwhile, patient Bob is about to receive rehabilitation therapy to improve his balance. The therapist sets Bob's game to target the player's torso as the input focus and weight displacement/center of mass as the key metric, again specifying how different thresholds of this value should be interpreted by the game. Though playing separately and for different therapeutic goals, both Alice and Bob are able to partake in therapy for their specific needs with only minor configuration of the same game that resulted from a single development effort.

5. System for Unified Kinematic Input (SUKI)

Game flow is a factor in maintaining player engagement and motivation and player engagement and motivation may be the key factors in driving successful patient outcomes in AVG therapy games. Said in an opposite way, poor usability will make game flow choppy and poor, which in turn may lead to poor therapeutic outcomes. It follows that usability is a factor that may ultimately influence patient outcomes in a therapy AVG.

Therapy AVGs, given their patient-driven goals, may create a bigger challenge because creating productive therapy games in spite of a player's potential impairment requires that designers take into account accessibility, flexibility, and versatility in body motion input.

The SUKI system described herein provides a set of tools for adaptive games.

5.1 System Overview

The SUKI system may address: (1) the inherent complexity of writing abstract routines for human body controls due to the breadth of the domain, and (2) the difficulty in designing input processing methods flexible enough to address a broad range of player physiology and therapy goals. Specifically the system may leverage the full expression of kinematic movement rather than a simple measurement of exercise output, allow for extensible end-user configuration for how player movement drives gameplay without requiring specific knowledge of computer programming, may not limit input configurations to movements predetermined by the developers, enable these changes to be made without the need of source code or recompiling the application, and can adapt its input processing based on the demonstrated individual capability of the player.

To achieve this, SUKI provides input abstraction library that decouples a game's interpretation of input signals from the body motion data reported by the kinematic sensor, where the two are linked by a user-defined text file loaded at runtime. This library file, which may be written in a JavaScript Object Notation (JSON) format but need not be so limited, may implement a schema that the SUKI system may use to convert measurements of a player's movement to values that can be consumed by a game software at runtime.

During development, the games are provisioned with abstract input anchors through which it can read these values from the SUKI system to drive gameplay. The SUKI schema design provides end users with a toolkit for defining custom movements based on angles and distances between areas of the player's body, aiming to be flexible and expressive while not requiring specific programming knowledge or experience. Users may thus create a multitude of JSON files that can be loaded and unloaded from the game at any time to change the relationship between player movement and gameplay on demand.

In overview of this system, a user provides kinematic data through the sensor to the game engine. In the system, the kinematic data registered by the sensor may not be directly interpreted by the game engine as in traditional AVGs. Instead, the game may be provisioned with abstract input anchor that serve values at runtime according to player movement and the prescribed interpretation defined in JSON schemas created by the end user. Schemas may be customized and loaded or unloaded on demand to change how player movement drives gameplay.

5.2 System Requirements 5.2.1 Motion Controller Programming

In traditional game development, namely those that use typical button or key-based controls, may include input routines where the task of writing for abstract input is straightforward and tools and practices exist for provisioning a game to support an array of controls. Even without developer intervention, operating systems provide system-level tools that enable players to remap commands to different keys or even different devices. These solutions provide some flexibility to gaming, particularly for players who may have intervening factors that prevent the use of a particular device or control configuration.

Similar conveniences do not exist for games that rely on human body movement to convey user intent. Not only are the routines for detecting input fixed, but the domain of expression in analog human movement is larger and more complex than that of a discrete-button controller or even a mouse and keyboard. This issue presents additional complexity when faced with the challenge of adapting a motion-based game for a player, whether attempting to remap the existing controls or to change the therapeutic goal of the activity entirely.

Figure 8:
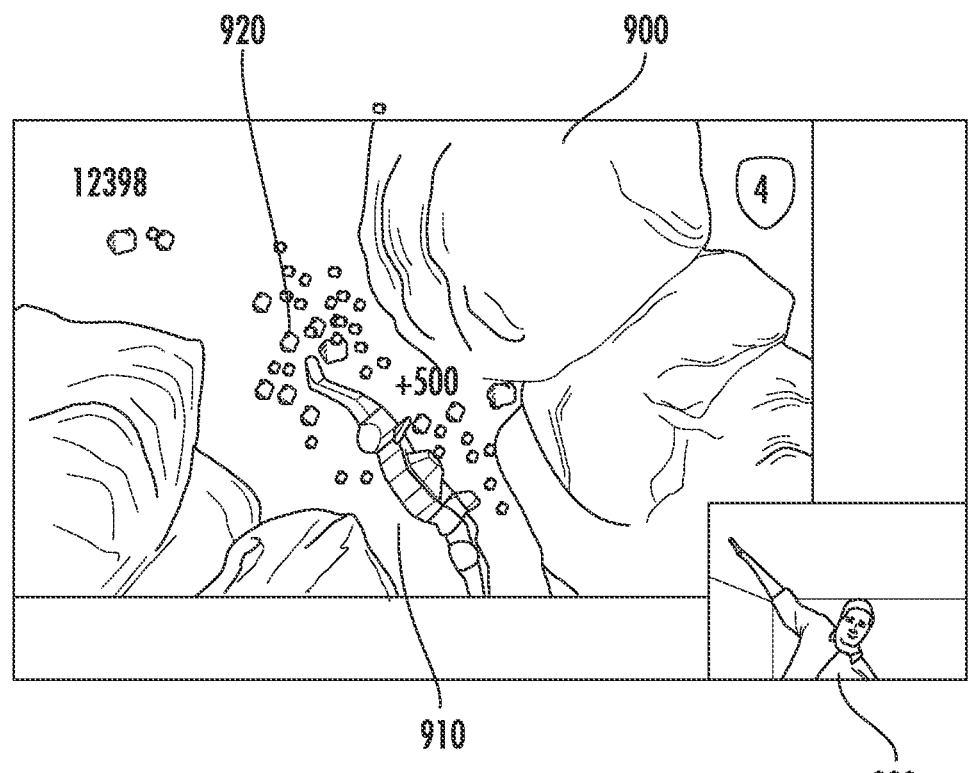
FIGS. 8 and 9 show gameplay screens overlaid with corresponding user interaction.
Figure 9:
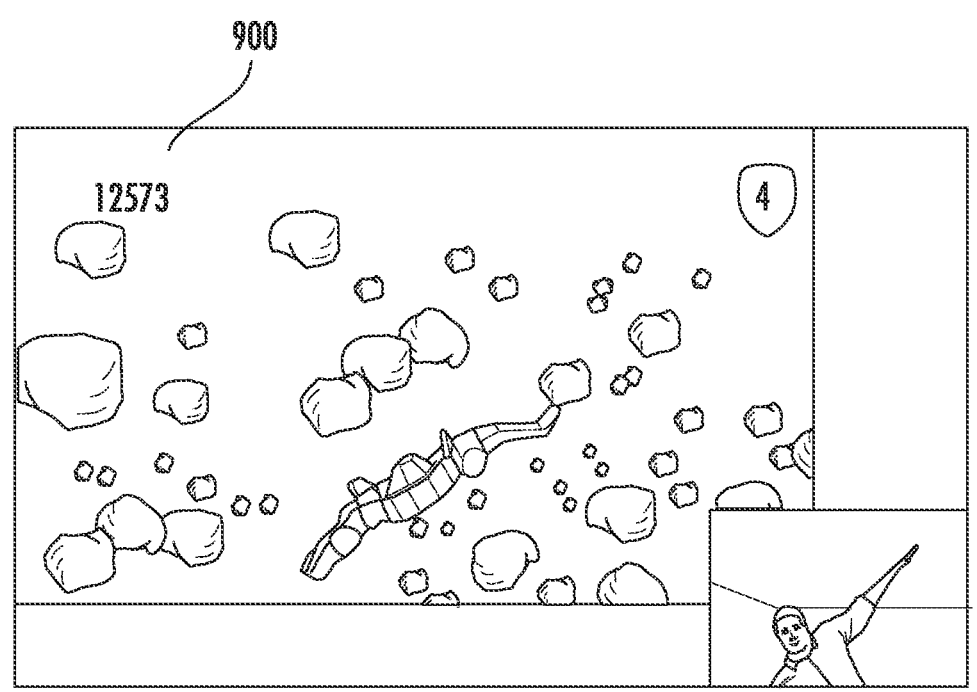

For instance, consider a game in which a player steers a spaceship through an asteroid belt (FIGS. 8 and 9). FIGS. 8 and 9 show a game screen 900 in which a ship 910 dodges asteroids 920. The ship 910's movements correspond to a user 930 (shown in the figure but not necessarily on the gaming screen) angling their arms to the left and right in correspondence with the ship 910. Consider a baseline game written to track the angle of the player's outstretched arms and match the tilt of the arms to the roll of the ship. But if a player with limited upper arm mobility wanted to play the game, the SUKI system allows for remapping the controls to follow the left or right lean of the player's torso, such that it might be valuable as a posture or balance control exercise for a player with Parkinson's disease.

5.2.2 Game Adaptation

Beyond remapping input controls and re-purposing games for new therapeutic use, another difference between traditional games and motion-based games is the specificity of control. Except for the analog joystick or trigger component on modern controllers, most button presses on a game controller register as a simple, singular event delivered to the program. Keyboard strokes and mouse clicks similarly are either pressed or released. Movement of the human body, in contrast, is naturally analog, and unlike with a controller, not every player has the same scope of input potential.

To provide better therapy, developers may provision AVG software with a variety of customizable options and parameters, but even establishing parameters for gesture detection and thresholds for movement assume that a set of pre-programmed input routines exist to watch for those gestures and evaluate those thresholds. If a player or therapist needed an adjustment that the developers had not predicted, they have no means by which they could make the necessary changes. The SUKI system provides an input logic for the game outside the application in a way that is configurable without requiring a modification to the game software itself.

Further, since this logic could be changed over time outside the game, the system itself may make these changes over time as it begins to understand the needs of the player. Though SUKI input configuration files may be managed manually by the therapists and players, one solution may also demonstrate the use of adaptive game techniques to fine-tune the challenge of the activity based on a knowledge of the player's capabilities as recorded in their unique profile.

SUKI contributes to this area by providing a method for adapting a game's input requirements based on knowledge gained regarding the player both ahead of time and during gameplay.

Figure 10:
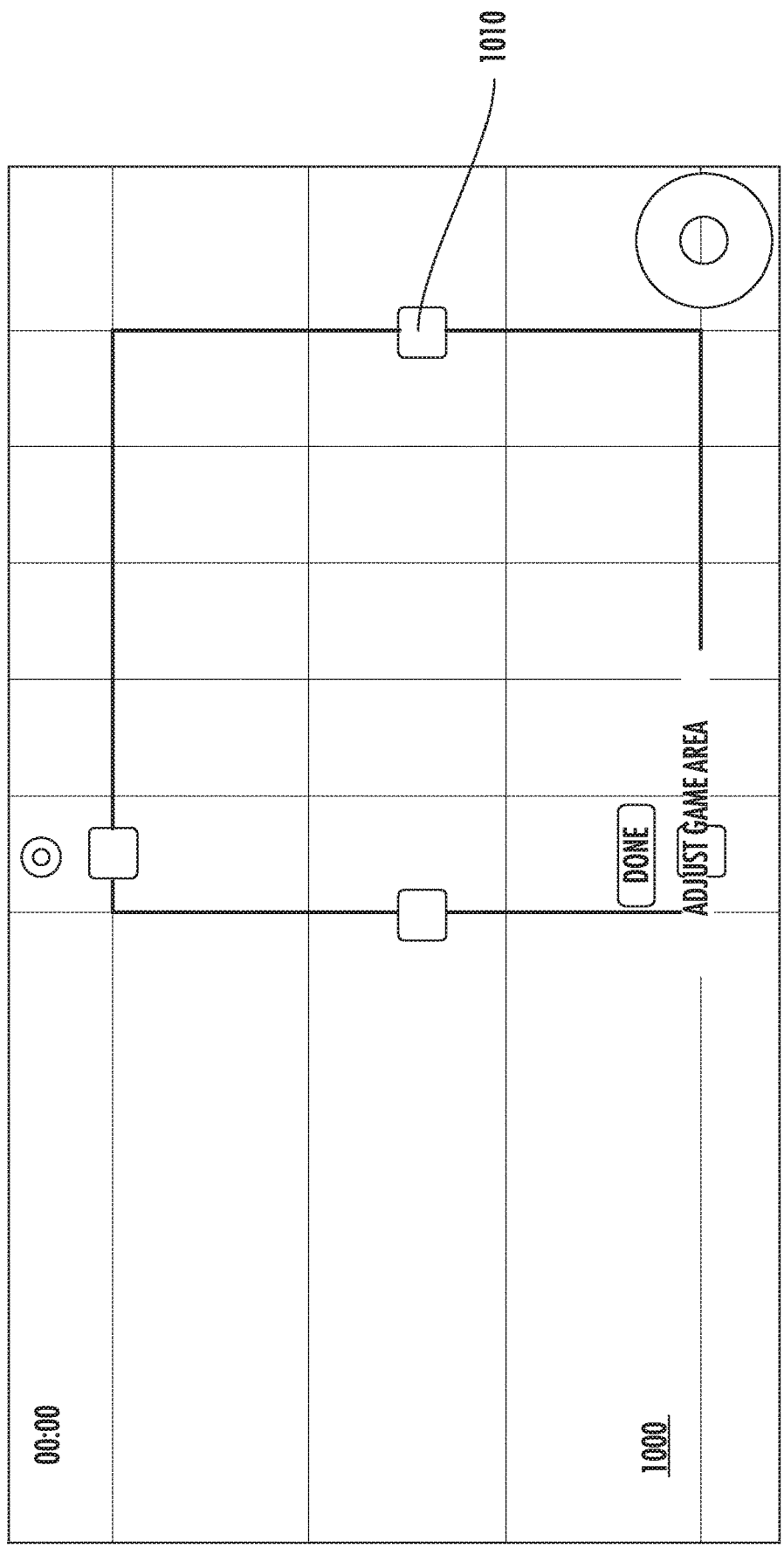
FIG. 10 shows an alternate calibration screen.

FIG. 10 shows an example of this adaptability similar to FIG. 7. As shown in FIG. 10, a therapist has calibrated the game for a patient with limited use of their left arm by setting boundaries of game play that takes place in the entire screen 1000 within the boundary 1010. Game activity will thus take place within the designated area on the right side of the screen 1010 to keep gameplay engaging. With SUKI, this boundary 1010 may not need manual adjustment; instead, it can develop over time after observing the player.

5.2.3 SUKI Design Parameters

The SUKI design may include at least the following design parameters:

Abstract Input: Enable developers to write input routines that are abstracted and decoupled from the particular motion capture device or anticipated gesture.

No Recompiling: Enable therapists to modify the gameplay experience toward customized therapeutic goals without any change to the game's code.

Patient Individualization: Allow the input to be tuned or calibrated to meet the physical capabilities of the individual patient.

Compound Metrics: A modular, flexible system that allows for the application of multiple schemas at once.

Runtime Updates: Schemas can be updated at runtime to affect gameplay immediately.

Ease of Integration: A portable, reusable software library that new and existing AVG projects can easily import and integrate.

5.3 System Architecture

The following is an overview of the architecture of the SUKI framework from the perspective of the developers who may implement it in their applications and the users who may configure custom schemas to address their individual therapy goals.

5.3.1 Overview

Figure 11:
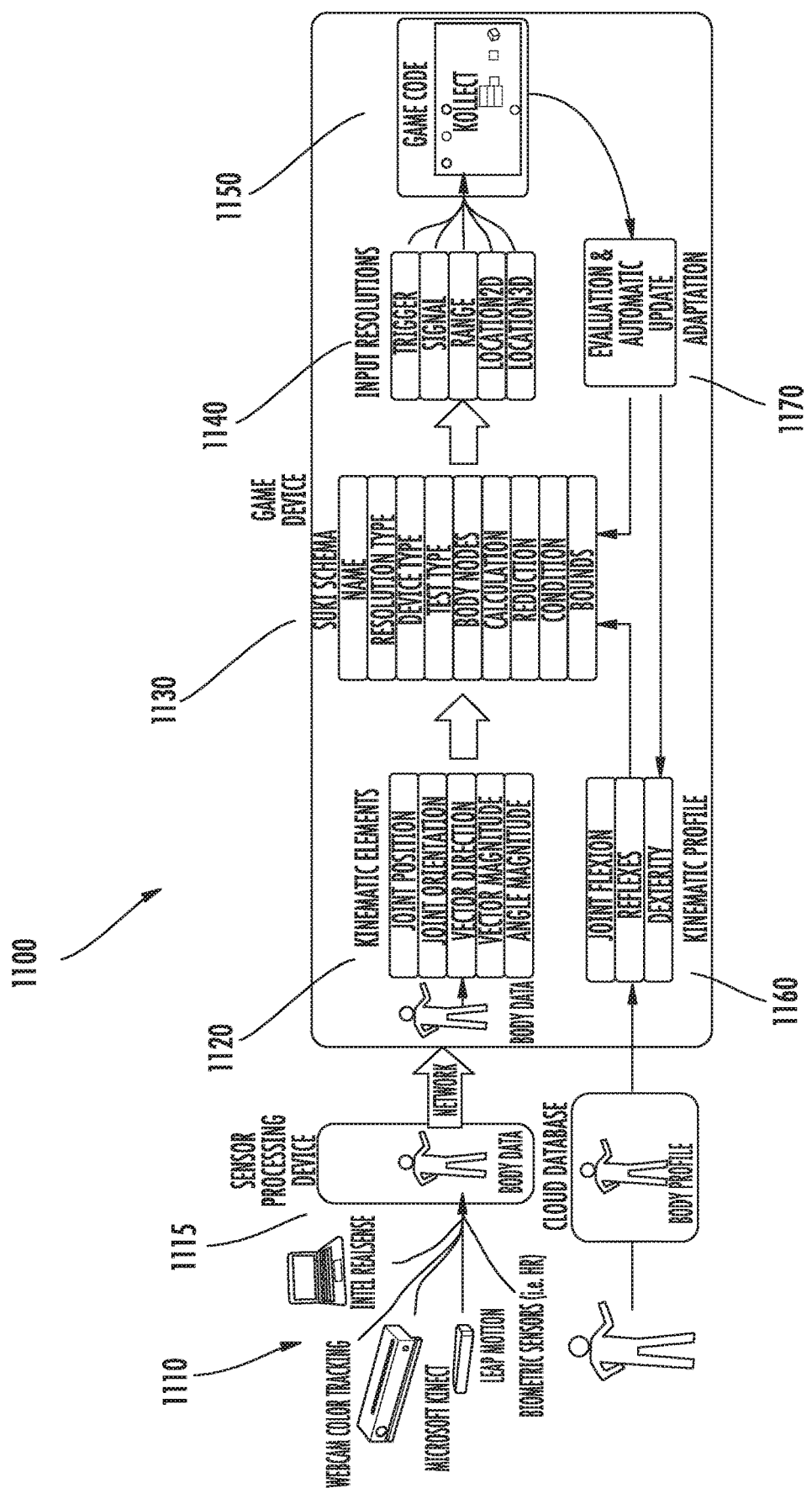
FIG. 11 shows a simplified overview of SUKI system architecture.

The SUKI system 1100 may include three component modules as illustrated in FIG. 11: the kinematic elements 1120, the SUKI schema 1130, and the input resolutions 1140. Input sensors 1110 provide body data to be processed by the system through a sensor processing device 1115. The system 1100 may create create kinematic elements 1120 in a unified format for system processing. The kinematic elements 1120 may include body-related elements such as joint position, joint orientation, vector direction, vector magnitude, and angle magnitude. In addition, although originally developed for kinematic inputs, this architecture is not limited to only kinematic inputs. Any vector-based body-data (such as biometric inputs including heart rate or oxygen sensor data) can be used as input. The body data from one or more sensors can be aggregated into a common body data representation by a computing device and transmitted to the game device via a network as the common body data. This permits new sensors to be added without changing the game code, and for games to be run on devices that don't support body sensors, such as mobile devices or VR and AR headsets.

This aggregator can additionally serve as a launcher and patcher of the games that are driven by the body data. Input Resolutions 1140 may be defined by developers and integrated into the game and may include trigger, signal, range and location fields that can then be communicated to the game code 1150 in the form of gaming commands. The SUKI Schema 1130 acts as a schema between the kinematic elements 1120 and input resolutions 1140 and adds operators that can manipulate the data as it passes between the body motion data sensor and the game software, such operators including calculation, reduction, condition, and bounds. The schema 1130 receives organized body data fields data from the kinematic elements module 1120 and after manipulation, outputs an input resolution command corresponding to the organized body data. The body data fields can abstract the body data from the device and an optional network interface to pass body data fields from the sensor computing device to the gaming computing device.

The kinematic elements (or other biometric elements) are an organizational set of the information a program can expect to receive from a kinematic or biometric sensor device. The input resolutions are a set of abstracted user signals with which developers can provision their game in anticipation of integration with motion-based inputs. The operators within the SUKI schema describe the manipulations that should be performed on the kinematic elements 1120 before they resolve into input commands. The particular relationships among all components are defined by the SUKI schema 1130 (which may be implemented as a JSON string), which can be loaded and unloaded on demand to alter the game's behavior concerning player input.

The following sections describe each of these in more detail.

5.3.2 Input Resolutions

The modified signals from the kinematic sensors may be resolved to commands within the game according to categories of information that users convey to computer systems to implement control and indicate their intent to that system. To address this, the system organizes the types of information that a typical game would require from a player, regardless of the device or modality that facilitates that communication.

These types of information may be called user intents or input resolutions that may be supported by SUKI and include at least the following:

Inputs Conveying Timing and State Information:

Trigger. A simple event that "fires" once and is immediately reset. A trigger does not carry additional data but by its nature inherently conveys temporal data concerning the moment in which it fired. An example of a trigger input used in games is a command from the player for their avatar to jump at a specific moment in time, perhaps by pressing a button at that same moment.

Signal. A trigger that is not necessarily reset after it fires, but must be explicitly reset. A signal can be used to indicate a binary state (on or off) over time and can also be regarded as a compound trigger (i.e., two signals that indicate a change in state). An example of a signal may be a command from the player for their avatar to sprint, perhaps instructed to begin with a button press and end when the button is released.

Inputs Conveying Numerical Data and Value Information:

Range. A value on a continuum between two bounds. SUKI normalizes range values to a floating-point value between zero and one (inclusive). An example of a range may be the degree to which the player commands a virtual vehicle to turn, perhaps as conveyed by the horizontal offset of an analog joystick.

Location. A coordinate for a position in 2D or 3D space. A location can also be regarded as a compound range (i.e., multiple range values in aggregate). Like ranges, in SUKI all location axis values are normalized to floating point values between zero and one (inclusive). An example of a location input may be a command from the player to fire their weapon at an object on the screen, perhaps communicated as a mouse click or a touch on the screen at that object's location.

This set of input resolutions attempts may serve the player control needs in a video game; however, additional categories may exist. For example, one could argue that array information (e.g., a string representation of a voice command or an audio stream produced by singing) could be used as input into a game but could not be implemented using the categories above. Conversely, some of these proposed counterexamples could be regarded as a compound or aggregated grouping of the types listed above. Further examination and addition of one or more of these fundamental types may enhance the coverage and applicability of this taxonomy.

By invoking these four input types, developers can declare input resolutions in their software with unique names that register in the system and become available by named reference. With a SUKI library built for the a game development engine, developers may query for the values of their provisioned inputs in an Update( ) or FixedUpdate( ) function called each time the graphics engine or physics engine renders a new frame of the game. The code listing below shows an example of what the developer code might look like when querying the SUKI library for the values of provisioned input anchors for each of the above types.

Code:

```
void Update ( ) {
// cause the character to jump if triggered
if ( Suki . GetTrigger (" Jump ")) {
mainCharacter . Jump ( );
}
// raise / lower shield depending on signal state
bool shouldRaise = Suki . GetSignal (" ShieldUp ");
if ( shouldRaise && ! shield . IsRaised ) {
shield . Raise ( );
} else if (! shouldRaise && shield . IsRaised ) {
shield . Lower ( );
}
// shoot fireball at speed queried from range input
if ( Suki . GetTrigger (" Shoot ")) {
float firePower = Suki . GetRange (" Firepower ");
StartCoroutine ( ShootFireball ( firePower ));
}
// move a pointer on the screen
Vector2 2 Dtarget = Suki . GetLocation2D (" Pointer ");
pointer . transform . position = ScreenCoordinates (2 Dtarget );
// move light source to the 3D location
Vector3 3 Dtarget = Suki . GetLocation3D (" Light ");
light . transform . position = WorldCoordinates (3 Dtarget );
}
```

5.3.3 Kinematic Elements

Within the SUKI library, the term node may be used to describe one of many pre-defined locations on the body tracked by a motion input sensor or mapped onto a common human data representation. For example, the MICROSFT KINECT™ v2 tracks 25 individual nodes (called "joints" in the KINECT nomenclature). The player skeleton refers to the full set of all nodes reported by the sensor or calculated on the common human data representation. For example, joint angles can be calculated based on position data from a sensor, or even inferred using Inverse Kinematics when only end-effectors (such as hands) are tracked.

The term frame describes a snapshot of the player's kinematic data at a particular moment in time. The frame contains information for the entire skeleton, including positions and orientations of every defined node. Motion input devices usually capture these frames at a constant rate. For example, the KINECT v2 processes frames at 30 Hz.

The following are Kinematic Elements of the player skeleton on which SUKI may perform measurements each frame:

Node Position. A vector describing the position (x, y, z) of a node in 3D space. For example, this might track the 3D coordinate location of the player's head.

Node Orientation. A Euler angle describing the orientation of a node in 3D space. For example, this might track the direction the player's right palm is facing.

Vector. Between A vector describing the relative position (x, y, z) of one node to another. For example, this might track the vector formed between a player's hand positions in 3D space. From this value, we can measure either the direction between the nodes or examine the scalar value (length) to determine the distance between the two nodes.

Angle Between. The angle formed between two nodes relative to a third node, thereby forming a node triad. For example, a node triad may be formed by the right shoulder and right wrist nodes with a connection at the right elbow node. This measurement would calculate the angle formed between the RightElbow−+RightShoulder vector and the RightElbow−+RightWrist vector, thereby yielding the flexion of the player's elbow. Though most often constructed using nodes adjacent to each other on the skeleton, SUKI supports node triads of any three arbitrary body nodes (e.g., left hand and right-hand positions relative the head) if noted explicitly in the schema.

5.3.4 SUKI Schema Components

The Input Resolutions and the Kinematic Elements may be brought together at runtime by a SUKI Schema, which exists as a simple JSON string retrieved from a database or read from a file located on disk alongside the compiled game binary. The user specifies the file (or files, in the case that they deploy multiple schemas simultaneously) at runtime. Schema files can be edited, removed, and reloaded on demand, enabling the player or therapist to customize as needed the way the engine interprets input to the individual player's physical capabilities and therapeutic goals.

As the schemas attempt to distill raw player skeleton data into signals of the player's intent, each one defines a discrete player movement that will potentially resolve into an input signal for the game. SUKI implements these movement definitions as a collection of several attributes:

The number of nodes it observes (single or multiple)

The aspect or relationship of the node(s) it evaluates (position, orientation, vector-between, etc.)

The type of Input Resolution it will target (range, etc.)

The metric of the aspect or relationship it will evaluate (magnitude, direction, x-component, etc.)

The observed metric's data type (i.e., vector, scalar)

Additionally, there are a few special considerations that for particular schemas, depending on their construction:

A preparatory adjustment required for the metric prior to evaluation (offsets, scaling, etc.)

An action to be taken on the resulting value (signal setting, value normalization)

These attributes are further organized and expanded upon below to explain the design of the SUKI schema structure:

5.3.4.1 A & B Node Metric

The number of nodes observed and the features of those nodes to be evaluated may be related; therefore, the A and B nodes may be combined into a compound metric called the Node Metric. The Node Metric, or the combination of node count and characteristic of the node(s) measured, classifies every SUKI schema into one of four categories:

Position Vector describing position of a single node
Orientation Vector describing orientation of a single node
VectorBetween Vector describing relationship between two nodes
AngleBetween Scalar value describing the angle in a node triad

5.3.4.2 C Input Resolution

The second defining element of a schema is its Input Resolution, which determines what fundamental input representation the schema will render in the application. As described in Section 5.3.2, these are listed here again to emphasize the type of data that they generate:

Trigger. An event with no additional data other than the time it was created.
Signal. A boolean value indicating whether a state is active or inactive Range A floating point value between zero and one
Location2D. A 2-dimensional vector
Location3D. A 3-dimensional vector

5.3.4.3 A & B & C Node Metric+Input Resolution

Each schema may be classified by a joining of its Node Metric and its Input Resolution. For example, a schema that raised a signal when the player's right hand was within 0.5 meters of their head would be a "VectorBetween Signal" schema. A schema that fired an event whenever the player's left palm faced upward would be an "Orientation Trigger" schema. This categorization results in a total of 18 valid schema subtypes, with two of the potential permutations excluded because the AngleBetween node metric yields a scalar and is not eligible for location resolutions. The table shown in FIG. 12 displays the Node Metric and Input Resolutions that may be combined to form a valid schema.

5.3.4.4 D & E Reduction

For every Node Metric+Input Resolution permutation, an element or aspect of the node metric may be to observes and resolves to an input intent. This decision will also require a determination regarding the data type of the resolution; for example, a trigger or signal will expect a boolean (to fire in the former or to indicate the current state in the latter), a range will require a floating-point value, and so on.

The schema's reduction operator may be responsible for performing this conversion from a vector-based schema to a scalar-based resolution. For example, consider a game avatar with variable running speed that the therapist wishes would be faster the further the player extends a leg to the side outward from his or her body. The appropriate schema might monitor the vector between the player's pelvis and right foot nodes but would want to reduce the vector to just its 'x' component before yielding a range input value. Similarly, consider the laser gun on a spaceship that the therapist wishes would only fire when the player rotates his or her left palm toward the screen (and sensor). The schema might monitor the orientation of the player's left hand but would want to calculate the dot product between the hand's orientation and the forward vector k̂ to yield a scalar value indicating how closely they are aligned.

Note that schemas with location data resolutions cannot employ a reduction operator to reduce the node metric's output vector to a scalar value. Also, because the node metric for an AngleBetween schema is already a scalar, it also cannot use a reduction operator.

5.3.4.5 F Calculation

Before the reduction is applied, transformations on the node metric's vector can be performed using a Calculation operator, which could normalize or re-center a vector, find a cross product, or scale the vector before other operators are meant to process it. Calculations apply only to vector node metrics, so they are not available on AngleBetween schemas. However, they are available (and optional) for all input resolutions on all other schemas.

An example of a pre-reduction vector calculation would be subtracting a z-value of four to re-center a position vector to four meters in front of the sensor. Another example might be to calculate the cross product of a vector between two nodes and the upward vector ĵ to isolate a patient's limb movement within a physiological plane.

5.3.4.6 G Conditionals & Bounds

Triggers and signals may require a test (or Conditional operator) to determine whether or not they should respectively fire or raise. Similarly, ranges may be normalized to a value between zero and one using the extents defined in a Bounds operator. The same applies to location (both 2D and 3D) resolutions so that their components lie between zero and one.

An example of a conditional might be to fire a trigger if a distance between two nodes drops below a threshold. A schema's bounds field might call for normalization of the angle of the elbow (e.g., bounded at 30-150 degrees) to a range value between zero and one.

5.3.5 SUKI Schema Restrictions

The previous section discussed the information required by a schema to effectively associate the input resolutions provisioned in the game by the developer with the kinematic elements available via the body motion input device while providing the flexible elements (operators) required to define adjustable relationships between them. As noted, not every schema type can employ each of the four operators.

FIG. 12 shows a table that notes which components are required, restricted, or optional with each Node Metric+Input Resolution permutation.

5.3.6 SUKI Schema Definition

The code listing below contains the basic JSON definition for the SUKI Schema. As discussed later, some operator fields have additional sub-fields that engage the profile and adaptation engine.

```
{
"name" : "UniqueIdentifier" ,
"resolution" : "ResolutionType" ,
"device" : "DeviceName" ,
"metric" : "MetricType" ,
"nodes" : [ "NodeName" , ... ],
"calculation" : {
},
"operator" : "VectorOperator" ,
"vector" : { "x" : 0.0, "y" : 0.0, "z" : 0.0}
"reduction" : {
},
"operator" : "ReductionOperator" ,
"vector" : { "x" : 0.0, "y" : 0.0, "z" : 0.0}
"condition" : {
},
"operator" : "ScalarOperator" ,
"scalar" : 0.0,
"percentage" : 0.8
"bounds" : {
}
"low" : 0.0,
"high" : 0.0,
"extents" : Boolean
}
```

Implemented as a simple text file, the elements of the SUKI schema may be available for modification by the end-user (player or therapist) and enable customization of the gameplay experience without any change to the game software. FIG. 14 contains a description of the elements and applicable values recognized by the system for each.

The developers set the name and resolution fields that associate the schema with an input anchor they have provisioned in the software. The device, metric, and nodes fields tie the schema to the kinematic elements established in the SUKI library integrated by the developer within the game. What remains are the calculation, reduction, condition, and bounds operators, which provide the additional flexibility and expressiveness required to satisfy the large number of potential end-user scenarios.

5.4 Player Modeling and Adaptation

A flexible input system partially solves the problem of individualizing gameplay experiences for every user according to their therapeutic goals. Among players that may be seeking the same type of exercise, and therefore the same physical movements tied to gameplay, there may be variance in personal abilities to negotiate and execute those movements.

In pursuit of maximizing flow and player motivation in AVGs, SUKI's adaptability beyond its schema flexibility and the types of movements may provide value beyond what has been previously discussed. With a focus on adaptive game systems and player capability as a basis for dynamic adaptation, SUKI may incorporate knowledge of the individual player in its measurements and analysis to provide a more individualized and targeted experience.

5.4.1 Overview

Figure 15:
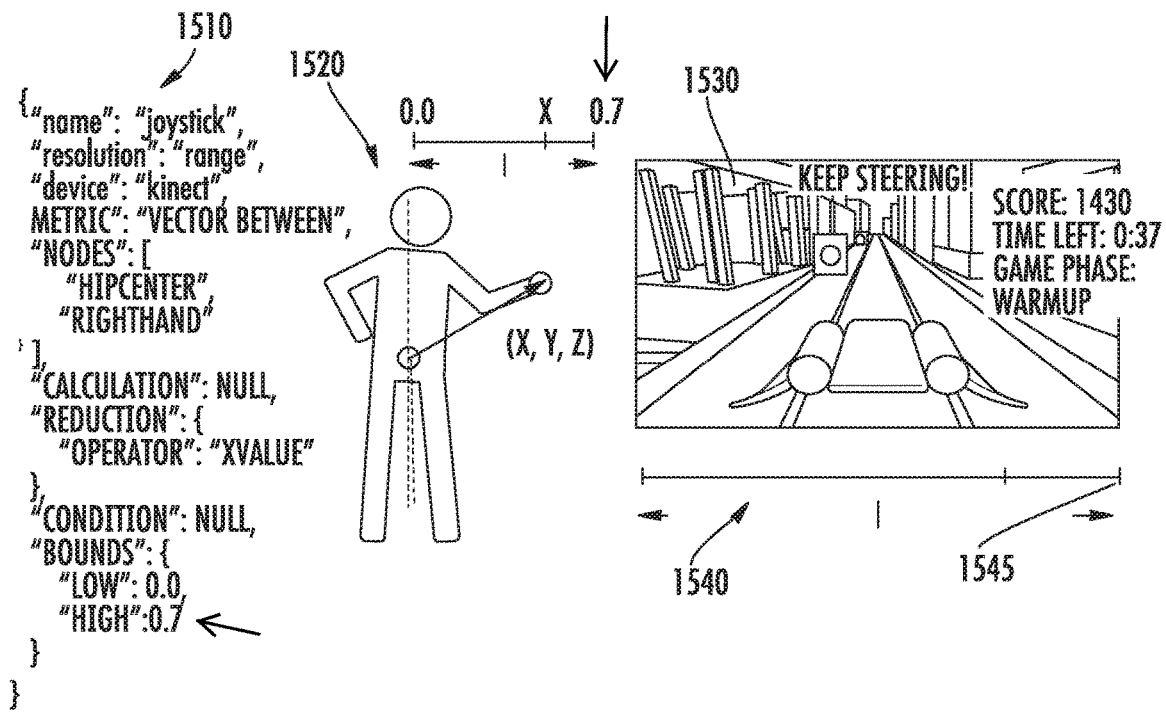
FIG. 15 shows an example that convert's a player's lateral reach into movement in a game.

Consider a schema that measures a player's lateral reach and converts it into a range value called "joystick" in a spaceship flying game to steer the ship, as illustrated in FIG. 15. To perform the range conversion, the schema requires a defined bounds within which to normalize the distance the player was able to reach. In an example working with patient, for example, with reduced upper body motility, the therapist may set this bound's extent to 0.7 meters (shown in the code 1510, patient graphic model 1520, and below the game screen 1530 as a boundary 1545 on a boundary scale 1540) as an optimal and challenging range for that patient. The patient plays the game, pulling her arm inward and pushing it out to the side while leaning to control the ship on screen.

Over time, the therapist may encounter two issues. The first is observed when the therapy improves the patient's balance and motility over time, enabling her to reach farther than the original extent set in the schema. The second is encountered when the therapist deploys the same schema for new patients with similar conditions and therapeutic goals. One of the new patients is an exceptionally tall adult male and is not challenged by the same distance setting, and the second is an adult female who experienced trauma in her elbow and finds that normalizing the play range over 0.7 meters is far too challenging. In all cases, the therapist could manually update the schema file, but an adaptive system based on knowledge of the player not only would improve the schema's usefulness across patients but would ensure that it provided an optimal and challenging experience within-patient even as that individual patient's capabilities changed over time.

The adaptation feature provided by SUKI can address this problem. As illustrated in FIG. 11, this system may include two additional components. The first is a persistent player model kinematic profile 1160 that reflects the player's capacity to perform a schema's movement, which may be fed with body profile data that may include kinematic Range of Motion (ROM) limits stored on a cloud, and the second is a monitoring system 1170 within the game that can detect changes in this capacity and use this information to update the schema's interpretation and the player's model. These components can influence the system via the operators in the SUKI schema and are both explained in further detail in the sections below.

5.4.2 Kinematic Profiles

The SUKI kinematic profile 1160 may differ from typical player models in that it does not consider player preferences or predilections, nor does it examine a player's motivation. It may, however, take into account a player's anticipated capacity to perform the movement defined by a schema and work by taking measurements of the player's joint flexion, reflexes, fine motor accuracy, and other determinants of capability to derive an estimate for player capacity in the schema's defined movement. Alternatively, the player's extents may be measured as related to the minimum and maximum values demonstrated or achieved for a schema-specific movement.

Figure 16:
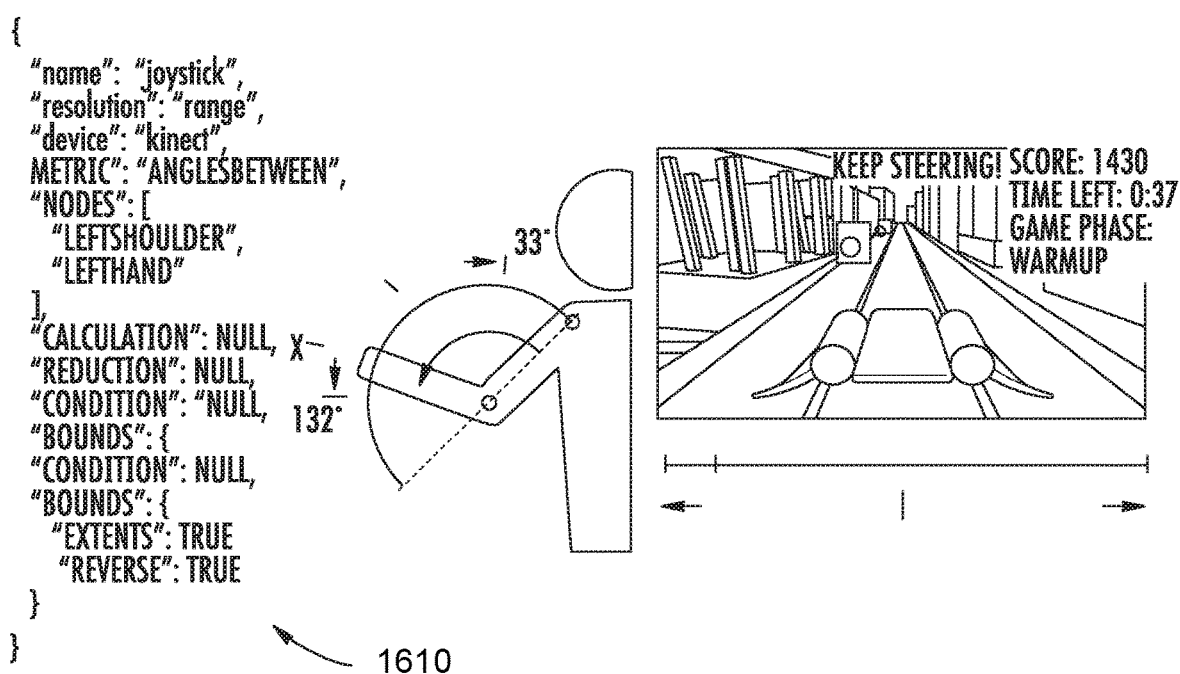
FIG. 16 shows an example that convert's a player's elbow angle into movement in a game.

Therefore, capability profiles may be unique for each player and schema combination; they may not generalize piece of information regarding the player, but by their nature are specific to the domain of the schema. Consider a scenario following from the side-reach example above in which a therapist works with multiple patients partaking in elbow flexion rehabilitation. The therapist creates the schema illustrated in FIG. 16 based not on an angle or specific measurement but allowing a patient's boundary of movement to be set at an extent limit 1610, where instead of measuring lateral reach, patients will change the angle of their left elbows (in this case independent of arm orientation), where joint extension will push the ship left, and flexion will pull the ship right.

Understanding both that different patients will have varying elbow flexion and that this capability will ideally improve in each patient over time, the therapist chooses to reference kinematic profile values (defined as "extent" 1610) instead of literal values to define the bounds within the schema. From observations made by SUKI during play, the profile for an example rehabilitation patient knows that she can currently extend her elbow to 132 degrees and can flex to 33 degrees. These values become the target range for the angle normalization, where the patient can play the game and engage in therapy until her capable range increases. A second patient demonstrates a maximum extension of only 104 degrees, but the unique kinematic profile associated with that patient will provide SUKI with an appropriately reduced normalization range.

In the current implementation, player profiles may be stored in a database and retrieved via authenticated endpoints securely and remotely at the start of each play session. Persistence of the profile data in a remote server may enable the profiles to be accessed and applied to any session the patient plays, regardless of location (e.g., at the clinic or in the home). Player profiles can include all information related to player abilities or capabilities including Range of Motion extents or maximum joint velocities, biometric limits such as maximum heart rate, biological limitations such as color blindness, and even cognitive capabilities such as n-back memory test results.

The concept of existing extents informing future schema values is partially realized in the fact that schemas define a distinct player motion that is applicable anywhere in a game where there exists an input resolution of the same type. For example, the schema for normalized left elbow flexion targets a range input called "joystick" 1710 in FIG. 17. However, in another game where a range input is meant to drive the force of a golf swing or the speed of a running avatar, the same schema could be applied by simply updating the name field to that provisioned by the developers for that input anchor. In this way, schemas can apply across games to link the same player motion to new gameplay mechanics, and the individual player profile will similarly transfer to the new game as well.

5.4.3 Adaptation System

The SUKI adaptation system differs from traditional DDA systems in that it does not examine player's performance relative to game objectives as a basis for adaptation. Instead, SUKI uses empirical, antecedent metrics regarding player capability as a proxy measurement for challenge and engagement, anticipating that aligning player ability to the challenge of the game will increase the likelihood for an optimal player experience.

Though therapy AVGs aim to leverage the intrinsically motivating element of games toward therapy and consequently have an incentive to maximize player motivation and engagement within the game, the underlying goal of a therapy AVG is ultimately to provide effective therapy. Therefore, an adaptation system that uses player capability as its basis may be more appropriate than one that merely observes in-game performance or behavior that is both limited to the domain of the game and a consequence of the interaction (rather than a predictor for that interaction). This decision also shares a foundation in therapy science, where therapeutic goals are optimally pursued by continuously tailoring therapy to the changing condition of a patient, especially in the case of chronic disabilities.

To that end, while player profiles provide flexibility in managing schemas and applying them to patient sessions, they would be limited if not provided the means to adapt to changing player capability. Therefore, the SUKI framework includes a component that monitors the player's demonstrated movement capability within the context of a schema to update the game and the persistent kinematic profile in real time as new physical movement extents are demonstrated to have been achieved by the player.

Figure 17:
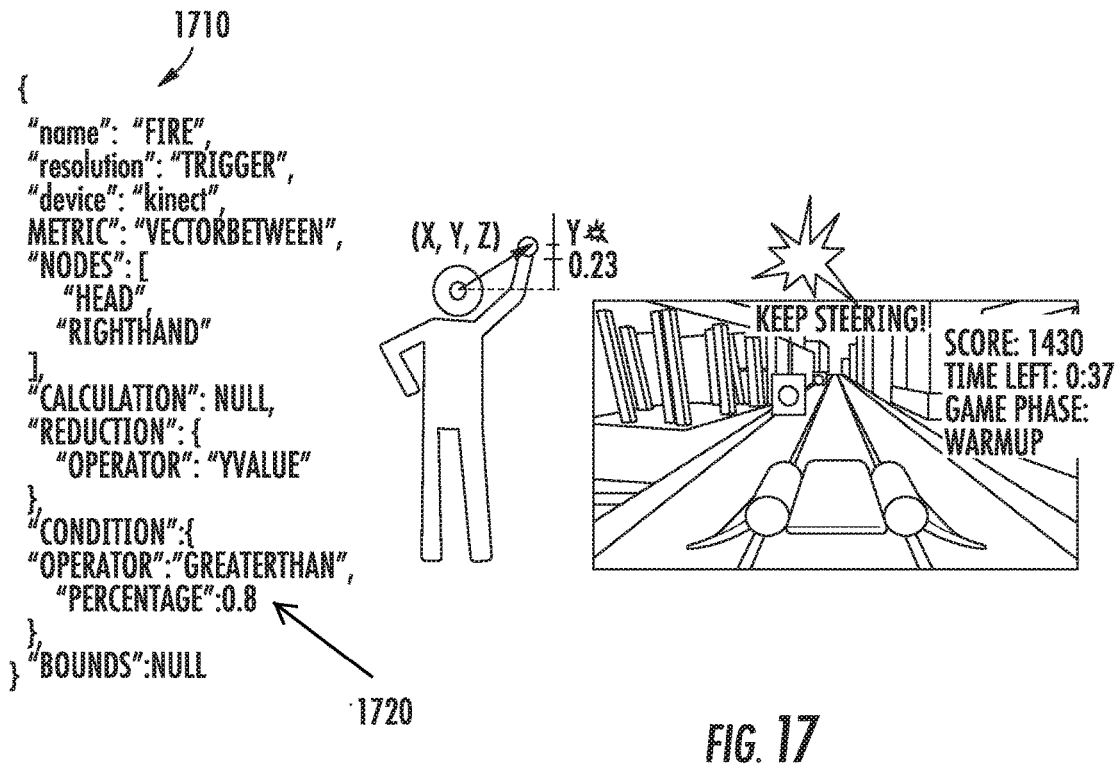
FIGS. 17 and 18 show an example where a player must hold a certain position to open another trigger in a game.
Figure 18:
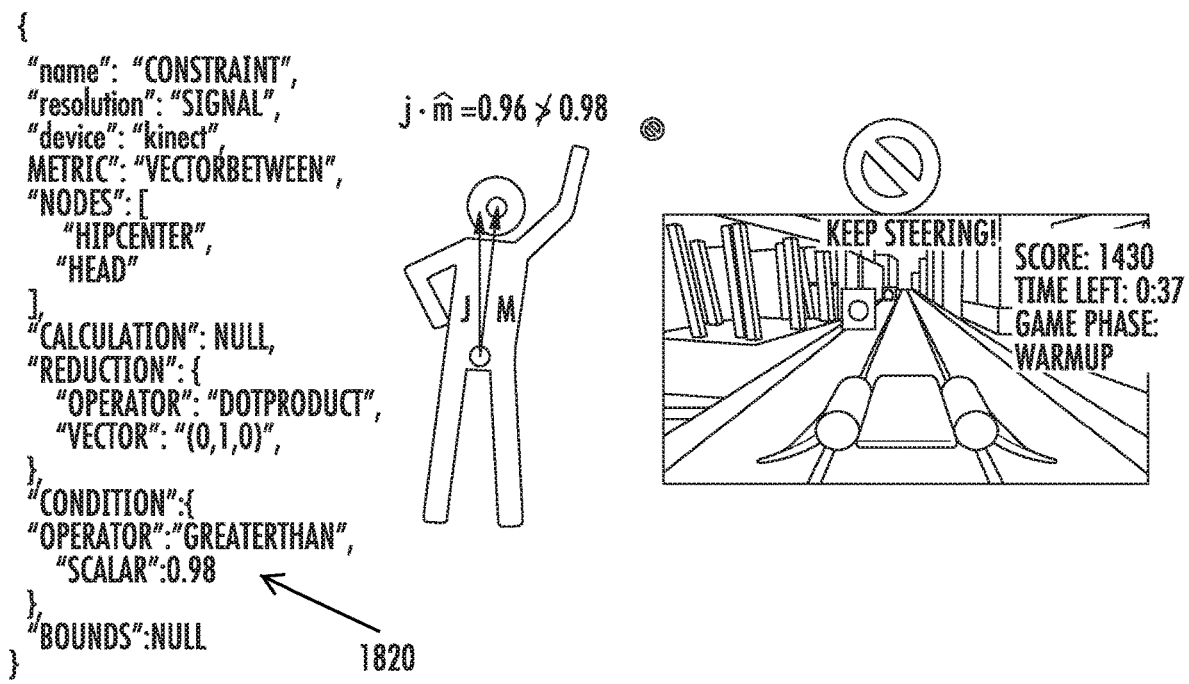

Consider the examples illustrated in FIGS. 17 and 18, where a therapist working with a patient with Parkinson's disease wishes to focus on upper body movement and posture simultaneously. In a game where the developer has provided a trigger input 1710 to fire the ship's main cannon, as a best practice they have also provided an optional signal input as a constraint 1720, 1820 that locks the cannon if a kinematic condition is not met. The therapist deploys two schemas concurrently: a trigger based on the patient raising his right arm above his head and a signal based on the player standing up straight without hunching forward or leaning to the side.

In the first schema in FIG. 17, a trigger input fires when the player reaches his right hand above his head beyond a threshold determined by his kinematic profile (80% of demonstrated maximum). The second schema in FIG. 18, used as a constraint, activates a signal input only when the patient is standing up straight. The use of the dot product reduction against the upward vector $\hat{j}$ allows this constraint to function whether the player is leaning forward, back, or to either side. The software may be programmed to trigger a notification and gameplay penalties unique to the game when the constraint is not satisfied (i.e., the constraint signal is not active); in this case, the ship's cannon will not fire regardless of the right hand's position. With explanation from their therapist regarding the nature of the schema, this compels the player to maintain an upright posture throughout the session while engaging in other directed movements.

As in the previous section, the first schema makes use of the extent reference when setting the threshold condition for the trigger input. By default, this would establish the trigger to only fire when the player exceeds their previously demonstrated maximum value for vertical reach. However, to promote more achievable gameplay goals, the therapist may engage an optional field in the schema available to the condition operator that sets the threshold to 80% of the maximum extent recorded in the player's kinematic profile.

As the player improves, new extents may be reached, thereby increasing the height at which this condition will fire the trigger. The SUKI adaptation system evaluates the resulting value from every schema calculation throughout the play session, and if the player achieves a new extent, that value will be updated in the current session as well as sent to the database for recording in the player's persistent kinematic profile. When the player starts a new session in the future, this updated value may serve as the starting benchmark for evaluating the trigger condition.

Some conditions for which individuals receive therapy are progressive, and it is reasonable that over time capability may not improve but instead decline. Over the long term, this may apply to certain traits even in players without any particular disability. In the current implementation, the kinematic profile for each player begins without assumption and determines its values through observation of the player; therefore, a reset of the kinematic profile for a player experiencing a reduction in capability serves as an effective solution at present. Therapists can perform this operation through an administration tool that interfaces with the database. In the future, the adaptation system may even be capable of detecting these regression trends over time and modify player expectations automatically.

Together, the persistent kinematic profile and adaptation system enable flexible schemas that support multiple users without the need to change the schema. They not only facilitate the tailoring of gameplay experience to every individual player, but they will continue to update that experience to match the player's capability as they achieve new therapeutic goals. Finally, with the ability to reuse schemas across games, this profile may be activated whenever the player engages this exercise movement, regardless of the particular game they are playing.

6. Evaluation

The first case study is an example using SUKI to construct a shoulder movement therapy AVG for patients with cerebral palsy (CP). The second is one in which that same game is re-purposed via the SUKI system toward an alternate therapy for an entirely different patient group. The third is one in which an existing therapy AVG developed traditionally with hard-coded input routines is retrofitted with SUKI and schema-based, adaptive input functionality to explore SUKI's potential for enhancing existing games.

In examining the case studies and the examples previously illustrated, the first two case studies show SUKI's capacity for providing a system that enables (1) Abstract Input with (2) No Recompiling that allows (3) Patient Individualization with support for (4) Compound Metrics that can be (5) Updated at Runtime. While these two cases will also demonstrate the (6) Ease of Integration into a game at design time, the third case study shows the ease of integrating SUKI into an application that has already completed its development.

6.1 Case Study 1: Constructing a Therapy AVG with SUKI

As demonstrated in a few of the design examples, SUKI was selected for implementation in an AVG therapy game that is a futuristic "endless runner" in which players guide a spaceship forward down a three-lane track, dodging obstacles and picking up power-ups. Designed for patients with CP, the exercise game encourages the use of the upper body to promote strength and movement planning.

6.1.1 Developer Integration

The primary control objective in the endless runner game is the movement of the ship left and right while it is automatically propelled forward down the track. To allow for maximum flexibility, there may be three movement modes within the game. The first mode treats each lane as a discrete position, where the player can input a "Placement" range value to indicate which of the three lanes they want the ship to fly in (i.e., 0.0-3.3, 3.3-6.7, 6.7-1.0). The second also views the track as three discrete lanes, where it moves between any two of them when receiving a "MoveLeft" or "MoveRight" signal input. The third considers the full track as an open field where the player can move in a more analog fashion anywhere they please (though the green and red blocks will still be generated to align with one of the three lanes). In this last case, the game reads a range value called "Joystick" and will move the player left and right according to the value's distance from the center (i.e., <0.4 to move left, >0.6 to move right, with a 20% "dead zone" in the center). To implement these movement modes, the developers include the code from the code below in their main game loop.

```
if (suki.RangeExists("Placement")) {
// range value to define three placement lanes float range =
suki.GetRange("Placement"); float leftMoveX = .33f;
float rightMoveX = .66f;
// move to L/M/R depending on the range value if (range < leftMoveX) {
MoveToLane(Position.Left);
} else if (range > rightMoveX) { MoveToLane(Position.Right);
}  else   {MoveToLane(Position.Middle);
}
} else if (suki.SignalExists("MoveLeft") &&
suki.SignalExists("MoveRight")) {
// pair of trigger values to move left or right bool moveLeft =
suki.GetSignal("MoveLeft"); bool moveRight =
suki.GetSignal("MoveRight");
// add a cooldown to the signals timeSinceLastLaneMove +=
Time.deltaTime;
// if there is a distinct direction signal active
if ((!moveLeft && !moveRight) || (moveLeft && moveRight) ||
(timeSinceLastLaneMove< LaneCooldown)) {
return;
} else if ( move Left) {
if (position == Position.Middle) { MoveToLane(Position.Left);
} else if ( position == Position . Right) { MoveToLane(Position.Middle);
}
} else if (moveRight) {
if (position == Position.Middle) { MoveToLane(Position.Right);
} else if ( position == Position . Left) { MoveToLane(Position.Middle);
}
}
}
timeSinceLastLaneMove = 0f;
} else if (suki.RangeExists("Joystick")) {
// range value as a joystick to move left and right float range =
suki.GetRange("Joystick");
// map 0 to 1 -> -1 to +1 with a deadzone (%) in the center float
xPercent = Suki.Utilities.Map(range, -1, 1, Deadzone);
// apply the left / right force to the ship float hForce = -xPercent *
MoveFactor; ship.AddForce(new Vector3(hForce, 0f, 0f));
}
```

This code creates four named input anchors (i.e., "Placement", "MoveLeft", "MoveRight", and "Joystick") that, with the "MoveLeft" and "MoveRight" combined, correspond to the three movement modes discussed above. These anchors can be referenced by a SUKI schema to provide specific information for how that input will be collected and responded to within the game. In this way, the input is abstracted and allowed to be defined by the external schema without any need to recompile the software.

The developer may also include a constraint input, so that users can optionally specify a movement or posture requirement the player must satisfy during gameplay. If the player's positioning in any frame does not satisfy the constraint, the game should implement a consequence with feedback (e.g., a UI or gameplay change). In this case, the developer changes the ship's color and disables movement of the ship if the constraint signal exists and is not active, placing the code below before the input interpretation code to exit the function early.

```
// only continue if defined constraints are met if
(suki.SignalExists("Constraint")) {
if (!suki.GetSignal("Constraint")) {
// change the ship ' s color to indicate error shipRenderer.material.SetColor
("_EmissionColor", error); return;
}
// change the ship ' s color back to normal shipRenderer.material.Set
Color("_EmissionColor", normal);
}
```

With the SUKI library included in the project and these code statements in place, the developers can compile the software and begin constructing SUKI schemas that target the abstract input anchors provisioned in their code. As a best practice, the developer should also include documentation of these input anchors for end-users who wish to construct custom schemas.

6.1.2 Schema Construction for Cerebral Palsy Therapy

For this example of a patient with CP, as with many neuromuscular conditions, the reported therapy treatments often target Activities of Daily Living (ADL). ADL behaviors are a set of meaningful activities that incorporate specific functional movements that reflect those a person would be expected to perform routinely in the course of self-care, including grooming, bathing, self-feeding, and so on.

The traditional set of ADL behaviors along with the broader Instrumental Activities of Daily Living (IADL) are often referenced as named tasks and subtasks such as Bring Oil to Pan, Bring Second Slice to Toaster, and Put Pan in Sink. Because many of these routine movements rely heavily on the patient's shoulder flexion and range of motion, arm movement is a prime consideration for many therapy routines.

To implement these movements as input into the endless runner game, three sets of schemas were created to respectively address each of three movement modes provisioned within the game. A therapist may not deploy all of these schema sets at once but rather would choose among these options depending on the intended exercise and therapy goals.

The first schema (below) reads the player's movement for the first exercise pattern (shoulder adduction and abduction) in the right shoulder to drive the "placement" input mode provisioned within the game.

```
{
"    name": "Placement", "resolution": "Range", " device " : " Kinect " ,
"metric": "VectorBetween",
"    nodes": [ "RightShoulder", "RightHand" ], "reduction": { "operator":
"XValue " },
"    bounds": { "extents": true }
}
```

It does so by reading the horizontal distance between the right hand and the right shoulder (relative to the sensor's camera space) to render a range value. Using extents to track the furthest distance achieved by the player, this schema may render a number between zero and one conveying the distance the player is currently reaching to the right bounded between their right shoulder and that extent. Extending the arm straight out moves the ship to the right lane, lowering the arm down will move the ship to the left lane, and holding the arm out at a central angle will place the ship in the center lane. The supervision of a therapist could ensure that the patient is maintaining proper form and secondary movement objectives while engaging the motion. Optionally, SUKI could also be configured to enforce that form within the game via the constraint signal. For example, a separate schema could be set to monitor the upright posture of the player and fire the constraint signal if the player leans too far while extending as discussed above.

The above scenario could also be implemented as an AngleBetween schema that monitored the angle formed in the node triad of the RightHand, RightShoulder, and Hip-Center nodes. This alternative schema could also pair with a constraint schema that ensured the normal vector of that triad was within a threshold of the forward vector $\hat{k}$ using a cross product calculation and a dot product reduction, thereby only registering the player's arm movement when performed in the proper physiological plane.

The second schema set below reads the player's movement for the second exercise pattern (shoulder flexion and extension) on both the left and right arms to respectively drive the "MoveLeft" and "MoveRight" inputs within the game. They do so by reading the vertical distance between the hand and the shoulder, the maximum of which the player can achieve only by raising the hand high over the head.

```
{
"  name " : " Move Left " , "resolution": "Signal", " device " :
" Kinect " , "metric": "VectorBetween",
"   nodes": [ "LeftShoulder"", "LeftHand" ],
"   reduction": { "operator": "YValue" },
"   condition": { "operator": "GreaterThan", "percentage": 0.8 }
}
{
"   name": "MoveRight", "resolution": "Signal"," device " : " Kinect " ,
"metric": "VectorBetween",
"   nodes": [ "RightShoulder", "RightHand" ], "reduction": { "operator":
"YValue" },
"   condition": { "operator": "GreaterThan", "percentage": 0.8 }
}
```

Once again, therapist oversight may ensure proper form (e.g., perhaps preferring a stretch of the arm forward and up rather than to the side), many aspects of which an optional constraint schema could also enforce within the game. Note that this scenario is an example of multiple schemas deployed simultaneously, creating a compound metric; by loading multiple schemas, separate kinematic data relating to the movement of the right and left arms can be interpreted independently to drive the gameplay.

This independence of input may be used where a patient may have reduced motility in one arm compared to the other. By referencing extents (i.e., "percentage") in the condition, these schemas will enable the players to move the ship right or left whenever they raise their respective arm above 80% of their previously demonstrated maximum for that arm. As a common consideration in some therapy scenarios, a player with reduced motility in one arm will not need to raise that arm as high as the other to achieve the same movement in the game.

A third schema reads the player's movement for the third movement mode (horizontal shoulder adduction and abduction) in the left arm to target the "Joystick" input anchor. It does so by examining the horizontal distance between the left hand and the left shoulder of the player.

```
{
"   name " : " Joystick " , " resolution": "Range", " device " :
" Kinect " , " metric": "VectorBetween",
"   nodes": [ "LeftShoulder", "LeftHand" ],
"   reduction": { "operator": "XValue" },
"   bounds": { "extents": true }
}
```

As the player moves the left outstretched arm sideways across and in front of the body, this will render a series of values that will normalize to a range between zero and one. Placing the arm near the center of that range will keep the ship stationary while moving it left or right will guide the ship left and right at a speed corresponding to the distance of the player's hand from that center point of the demonstrated capability range.

Note that this schema is similar to the schema presented earlier, where it similarly could be replaced with an Angle-Between schema that monitored the angle formed between the chest and the left arm. Similarly, this schema could pair with a constraint that ensured the normal of the node triad was within a threshold of the upward vector $\hat{j}$. Optimally, therapist oversight would also ensure proper ancillary form requirements while the game provided the motivation to engage in the therapy. For convenience, a simple UI in the game may allow loading and unloading schema files from disk. Using this UI, a therapist can add or remove these three scenario sets on demand from within the game, allowing a patient to engage in multiple therapy exercises within a single application launch.

This case demonstrates SUKI's ability to provide a system for abstracted input via named anchors in the game's input routines, which allows for updating the mapping between player body movement and gameplay at runtime without a need to recompile the game binary. It also demonstrates the use of schemas to target players seeking different exercises for therapy and the use of extents to individualize that therapy for varying patient capabilities.

6.2 Case Study 2: Re-Purposing a Therapy AVG Provisioned with SUKI

This study examines the potential and suitability for adapting AVGs provisioned with the SUKI library toward multiple therapeutic goals and patient needs.

6.2.1 Schema Construction for Parkinson's Disease (PD) Therapy

Patients affected by PD present with an array of symptoms, including tremor, slowed movement (bradykinesia), rigidity, stooped posture (camptocormia), delayed postural responses (resulting in an increased risk of falling), cognitive impairment, and others. Like CP, a frequent treatment for PD is physical rehabilitation therapy, which does not aim to affect the process of the disability directly but rather improve function by encouraging compensatory activities that promote increased strength and control in the same aspects that have been diminished by the disability.

Though its distinctive tremor is perhaps the most well-known symptom of PD, camptocormia is often the most prominent symptom at the time of diagnosis. Posture, balance, and reaching exercises are considered core areas for physical therapy in PD treatments.

Several PD exercise routines were mapped toward the endless runner game's gameplay objectives. With the camptocormia condition in mind, of particular importance was a requirement that the patients perform the movements with a straightened, upright posture. Therefore, this case created a constraint schema that would ensure the patients do not curve their backs forward as they may be naturally prone to do.

```
{
" name " : " Constraint ",
" resolution " : " Signal ",
" device " : " Kinect ",
" metric " : " VectorBetween ",
"nodes" : [ " HipCenter ", " Head " ],
" reduction ": { " operator " : " ZValue "},
" condition " :{ " operator " : " Less Than ", " scalar " : 0.2 }
}
```

The schema implements the constraint by measuring the z-axis component of the position of the player's head relative to that of their pelvis, verifying that the difference does not exceed a reasonable threshold in the forward direction. Note that side leaning may even be encouraged in some routines.

With the compensatory posture component in place, the additional therapy exercise movements need mapping to the named anchors provisioned within the game. Like therapy for CP patients, PD physical therapy often targets ADL function, which rehabilitation programs that combine activity-related exercises have been shown to improve.

Many patients with PD exhibit abnormal postural responses in the lower body to regulate balance, which interrupts the patient's ability to respond effectively to a center of gravity displacement. Therefore, exercises were presented that focus on balance during changes in center of gravity. The schemas below may implement these movements as gameplay input in the endless runner game.

```
{
" name " : " Placement ",
" resolution " : " Range ",
" device " : " Kinect ",
" metric " : " VectorBetween ",
" nodes " :[ " Left Foot " : " HipCenter "],
" reduction ":{ " operator " : " XValue " },
" bounds ": { " extents ": true }
}
{
" name " : " Joystick ",
"resolution " : " Range ",
" device " : " Kinect ",
" metric " : " VectorBetween ",
" nodes " : [ " HipCenter ", " Head " ],
" reduction " : { " operator " : " XValue " },
" bounds " : { " extents " : true }
}
```

Under the supervision of the therapist, the patient stands with feet planted at shoulder width. While maintaining a straight back, the patient is then encouraged to shift his or her hips left and right without moving either foot. With a focus on hip movement, the head and torso may even remain stationary but are allowed to translate with the player's hips if desired. SUKI monitors the difference between the horizontal location of the player's foot and the center of the pelvis, converting the current value within the maximum demonstrated extents to a range value for the "Placement" anchor. With the player's center of gravity balanced between the feet, the ship will move to or remain in the center lane, where shifting the center of gravity toward the left or right foot will move the ship to the corresponding lane.

In the leaning torso scenario presented in the second list just mentioned above, the range value is derived from the difference in horizontal position between the player's head and pelvis center. As the player leans sideways left and right, an extent range will develop within which the patient can guide the ship using his or her upper body as a virtual joystick. For variety in gameplay, the "Joystick" input anchor is targeted to allow the player to move freely among the lanes.

Additional PD exercises may focus on the opposed objectives of extending reach and maintaining balance. One such exercise is a cross-over reach, where players are encouraged to stretch an arm forward across the body and out to the opposite side of that arm's shoulder. The schemas below implement this movement for both arms.

```
{
" name " : " Move Right ",
" resolution " : " Signal ",
" device " : " Kinect ",
" metric " : " VectorBetween ",
" nodes " : [ " HipCenter ", " LeftHand " ],
" reduction " : { " operator ", " XValue " },
" condition " : { " operator " : "GreaterThan ", " percentage " : 0.8 ,
" reverse " : true }
}
{
" name " : " Move Left ",
" resolution " : " Signal ",
" device " : " Kinect ",
" metric " : " VectorBetween ",
"nodes " : [ " HipCenter ", " RightHand " ],
" reduction" : { " operator " : " XValue " },
" condition " : { " operator " : " GreaterThan ", " percentage " : 0.8 ,
" reverse " : true }
}
```

While keeping an upright posture via the constraint, the player is encouraged to reach the left arm across the body and out to the right to move the ship right. Similarly, reaching the right arm across the body and out to the left will move the ship left. Under the supervision of the therapist, twisting of the upper body is also encouraged to add additional balance consideration and maximize reach distance. In this way, the schemas differ from the approach in the CP scenario, where here the distance is measured from a central location within the body instead of the shoulder. Where the CP exercise intended to isolate horizontal abduction and adduction of the shoulder, these PD scenarios are meant to actively promote leaning in the upper body.

In both cases, the corresponding signal input triggers only when the player achieves a percentage of the previously observed extent. Note that the schema monitoring the right arm uses the "reverse" flag to mirror the calculations for the left side.

As with the CP therapy schemas, these three scenario sets can be added or removed on demand from within the game, allowing a patient to engage in multiple exercise routines without restarting the application.

This case study shows the potential for SUKI to enable a single application to target multiple disabilities and therapeutic goals.

6.3 Case Study 3: Integrating SUKI into an Existing Therapy AVG

A primary therapeutic goal in a game with floating objects to be captures is patient heart rate, encouraging a more active and frenetic play style over a methodical approach. In the game shown in play in FIG. 19B and in a calibration mode in FIG. 19A, an avatar 1910 representing the patient stands or sits in the center of the screen, where movements of the avatar directly mirror the movement of the player as detected by a sensor. Within the game, floating markers 1920 attach to the locations of the avatar's hands and feet; though the markers are locked in the xy-plane within the game, they can move around the screen as a result of the player moving his or her hands and feet and driving the same movement in the avatar representation. Each round, a set of objects 1930 will spawn and float around the avatar. The player can "collect" these objects by making contact with them via the markers. In some game modes, hazard objects also spawn as a way to generate an additional challenge and encourage more careful movement planning; the player attempts to collect all of the target objects while avoiding the hazard objects to maximize the resulting final score.

One limitation of the game's input routines rests in the fact that the markers adhere to the avatar's hands and feet in the center of the screen, restricting the game from taking advantage of the full horizontal screen space as shown in FIG. 19A. Additionally, if the patient has asymmetric capabilities for flexion and reach, it is possible to spawn objects that may not be reachable on a particular side. The game currently manages both concerns with a manual calibration square 1905 defined before the game starts, in which the user designates the areas in which objects may spawn. However, with an implementation using SUKI, this manual calibration may no longer be necessary.

6.3.1 Code Integration

Integrating SUKI into an existing game as described involved adding the library to the project and updating the input code in the main game loop. Written in the Unity game engine, the game manages the hand and foot marker locations using a custom game object with an input script and four child objects representing the four markers within the scene. The case's programming task was to update this input script to manipulate the position of the four markers according to SUKI input data, rather than avatar body position derived directly from the game's sensor.

With the world space origin near the center of the scene camera, the four markers usually cover separate zones within the screen. For example, the right arm is intended to be used to collect objects that appear in the upper right quadrant, and the left foot is meant to be used to collect objects that spawn in the lower left quadrant. Therefore, it was decided to bound the movement of the markers to specific areas of the screen to enforce this play style. This design was accomplished by pre-calculating screen rectangles for each zone in the script's Awake( ) function, as shown below.

```
// get the rect of the screen in world space
Vector3 botLeft = Camera.main.ViewportToWorldPoint(new Vector3(0, 0, mainCam.nearClipPlane));
Vector3 topRight = Camera.main.ViewportToWorldPoint(new Vector3(1, 1, mainCam.nearClipPlane));
// determine the widths and heights of the active zones float width = topRight.x; float hHeight = topRight.y; float fHeight = -botLeft.y;
// assign the rectangles for active zones of the markers rects = new Dictionary<Transform, Rect>( );
// Rect is (x ,y ,w , h) with (0 ,0) in bottom left corner rects.Add(lh, new Rect(botLeft.x, 0f, width, hHeight)); rects.Add(rh, new Rect(0f, 0f, width, hHeight));
rects.Add(lf, new Rect(botLeft.x, botLeft.y, width, fHeight)); rects.Add(rf, new Rect(0f, botLeft.y, width, fHeight));
// add a rectangle that encompasses the entire screen
rects.Add(this.transform, new Rect(0f, 0f, 2 * width, hHeight + fHeight));
```

With definitions for the four zones, the Update( ) function establishes four Location2D input anchors to move each marker within its respective zone. Additionally, there is a check for a constraint with a UI cue that changes the colors of the hand and foot markers so that a therapist may optionally add one. With a set of class variables, constants, and references to the four child objects (via their Transform components), the input code for the game using SUKI inputs is shown in below.

```
// check for constraint
if (suki.SignalExists("Constraint")) { if (!suki.GetSignal("Constraint")) {
ChangeMarkerColors(error); return;
}
ChangeMarkerColors(normal);
}
...
// mode 1: move each marker within its respective zone if
(suki.Location2DExists("LeftHand")) {
rect = rects[lh];
pos = suki.GetLocation2D("LeftHand"); newPos.x =
-pos.x * (rect.width) + rect.
xMax; newPos.y = pos.y * (rect.height) + rect.yMin;
lh.position = Vector3.Lerp(lh.position, newPos, 1f);
}
if (suki.Location2DExists("RightHand")) { rect = rects[rh];
pos = suki.GetLocation2D("RightHand"); newPos.x =
pos.x * (rect.width) + rect.
xMin; newPos.y = pos.y * (rect.height) + rect.yMin;
rh.position = Vector3.Lerp(rh.position, newPos, 1f);
}
if (suki.Location2DExists("LeftFoot")) { rect = rects[lf];
pos = suki.GetLocation2D("LeftFoot"); newPos.x =
-pos.x * (rect.width) + rect.xMax;
newPos.y = pos.y * (rect.height) + rect.yMin;
lf.position = Vector3.Lerp(lf.position, newPos, 1f);
}
if (suki.Location2DExists("RightFoot")) { rect = rects[rf];
pos = suki.GetLocation2D("RightFoot"); newPos.x =
pos.x * (rect.width) + rect.xMin;
newPos.y = pos.y * (rect.height) + rect.yMin;
rf.position = Vector3.Lerp(rf.position, newPos, 1f);
}
```

With schemas to drive the named Location2D inputs based on the player's hands and feet in real world space, the above implements the movement objectives originally presented in the game. However, to take advantage of SUKI's flexibility, a few more movement modes may be implemented based on additional input anchors following this code:

```
// mode 2: single marker with coverage for the entire screen if
[suki.Location2DExists["Joystick")) {
rect = rects [this.transform];
pos = suki.GetLocation2D("Joystick"); newPos.x = pos.x * (rect.width) +
rect.xMin;
newPos.y = pos.y * (rect.height) + rect.yMin;
rh.position = Vector3.Lerp(rh.position, newPos, 1f);
}
// mode 3: single marker driven by two range inputs if
(suki.RangeExists("JoystickX")) {
range = suki.GetRange("JoystickX");
// map 0 to 1 -> -1 to +1 with a deadzone (%) in the center float
```

```
percent = Suki.Utilities.Map(range, -1, 1, Deadzone); newPos.x +=
percent * MoveFactor;
rh.position = Vector3.Lerp(rh.position, newPos, 1f);
}
if (suki.RangeExists("JoystickY")) { range = suki.GetRange("JoystickY");
// map 0 to 1 -> -1 to +1 with a deadzone (%) in the center float
percent = Suki.Utilities.Map(range, -1, 1, Deadzone); newPos.y +=
percent * MoveFactor;
rh.position = Vector3.Lerp(rh.position, newPos, 1f);
}
```

In this way, there are three modes for movement. In the first set, the original gameplay movements were replicated by using four separate input anchors that enable each hand and foot icon to follow the player's movement of the corresponding body part.

In the second, a single Location2D input will act like a joystick, driving relative movement of a single marker that is navigated around the screen to collect objects. In the third, two range inputs also guide a single marker but isolate the magnitude of the movement between the horizontal and vertical axes. To support different therapy scenarios, an existing game parameter available in the settings determines which (if any) of the markers are active. In either of the last two input modes, the therapist may disable the unused markers for the left hand and both feet.

6.3.2 Schema Design to Replicate Existing Gameplay

The first provisioned input mode may need 4 schemas to drive the Location2D inputs "LeftHand," "RightHand," "LeftFoot," and "RightFoot" based on the location of the respective body part of the player in real life. To do so, use of a Position node metric that tracks the player's hands and feet, as demonstrated below may be required.

```
{
"     name ": "RightHand " , "resolution": "Location2D", " device " :
" Kinect " , "metric " : " Position " , "nodes": [ "RightHand" ],
"     bounds": { "extents": true }
}
{
"     name " : " Left Foot " , "resolution": "Location2D", " device " :
" Kinect " , "metric " : " Position ", "nodes": [ "LeftFoot" ],
"     bounds": { "extents": true, "reverse": true }
}
```

Figure 20A:
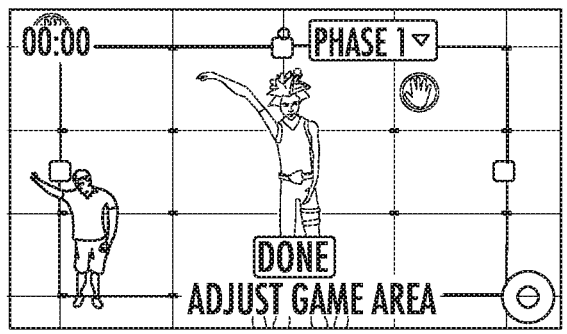
FIGS. 20A and 20B show different configuration screens showing movement boundaries.
Figure 20B:
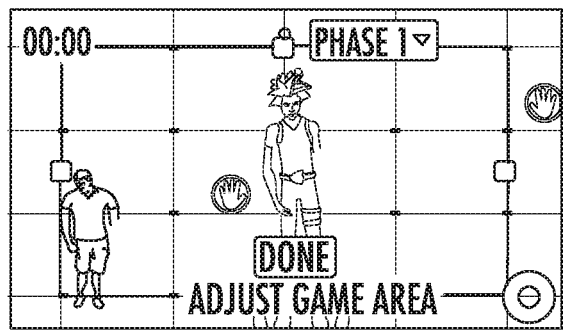

For brevity, only schemas for the right hand and left foot are shown, but similar schemas were also created to map input from the left hand and right foot as well. These four schemas together recreate the original input configuration for the game with a few improvements (FIGS. 20A and 20B). In the SUKI implementation of FIG. 20A, the player's hand and foot movements within their extents will map to the full size of the corresponding quadrant on screen and are no longer bound to the avatar. In the implementation of FIG. 20B, a patient with asymmetric arm movement capability will leverage independent extents. Note the mirrored right arm's limited horizontal extension moves the corresponding hand marker all the way to the edge of the screen.

First, because SUKI is considering the relative position of each body part within its observed extents and mapping them to an area of the screen, the entirety of the display can be used for gameplay. Second, because the extents for each body part are independent, the game will adapt to each body part according to the patient's capability. With these two improvements, the manual calibration square is no longer required, but may still be used if the therapist desires to control the locations of object spawns.

6.3.3 Leveraging SUKI for Alternate Play Modes

With SUKI now implemented for the traditional gameplay, the additional input anchors may be used to explore alternative play modes. In this example, the new exercises have not been designed to target a particular condition under the guidance of a rehabilitation expert but were constructed as a thought experiment to demonstrate the opportunities available in a game built with SUKI.

Where the current primary objective of the game being discussed is to increase movement and cardio output, there may be an opportunity to design a mode that focuses more on movement planning. For this mode, demonstrated in below, the "Joystick" input anchor that reads the player's right hand as a "virtual mouse" be used to guide a single marker around the screen.

```
{
"     name " : " Joystick " , "resolution": "Location2D", " device " :
" Kinect " , "metric " : " Position " , "nodes": [ "RightHand" ],
"     bounds": { "extents": true }
}
```

Moving the right hand up and down moves the marker up and down at a speed relative to the current vertical position between the player's demonstrated extents. Similarly, moving the right hand laterally in front of the body will move the marker sideways on the screen. In this mode, the player should attempt to carefully guide the marker to pick up target objects while remaining careful to avoid hazards.

As a second alternative movement mode, the isolated "JoystickX" and "JoystickY" input anchors may be used, where the magnitudes derive from independent range inputs. Considering the discussion above into balance exercises, a set of schemas may enable players to use their upper bodies as virtual joysticks to guide the single marker on the screen. In this scenario, implemented in the below code, leaning the upper body forward and backward at the hips would guide the marker up and down, and tilting side to side at the hips would guide the marker left and right.

```
{
"name ": "JoystickX", "resolution": "Range", " device " : " Kinect " ,
"metric": "Vector Between",
"       nodes": [ "HipCenter", "Head" ],
"       reduction": { "operator": "XValue" },
"       bounds": { "extents": true }
}
{
"name ": "JoystickY", "resolution": "Range", " device " : " Kinect " ,
"metric": "Vector Between",
"       nodes": [ "HipCenter", "Head" ],
"       reduction": { "operator": "ZValue" }
"       bounds": { "extents": true }
}
```

Whether or not these movement scenarios would be useful in AVG therapy for a particular patient and disability would be for a therapist to determine, but these examples serve to demonstrate the ability for SUKI to extend the potential of an AVG to support more varied exercise opportunities without recompilation than those created with traditional programming methods for body motion input. Additionally, these schemas serve as an example of what end-user therapists would be free to create on their own to suit their needs for a particular patient or exercise routine. As demonstrated, this functionality enables the therapist to modify a very fundamental aspect of the game without requiring any modification to the software.

7. Additional Applications

Beyond Body Movement. SUKI as discussed herein focuses on musculoskeletal physical ability, such as movement planning and range of motion. Other aspects of player physical capability, such as visual acuity, reflex time, or dexterity may provide bases for adaptation, depending on the nature of the game it is augmenting. For example, a console first-person shooter could intelligently adapt to a player's thumb dexterity by automatically increasing or decreasing dead zone and sensitivity on the analog joystick, dynamically adjusting the degree of aim assistance, or modifying the timescale of the environment.

Beyond Physical Traits. SUKI need not be limited to physical capability, and other aspects of individual difference among players (e.g., cognitive, temperamental, lifestyle) might serve as viable bases for adaptation. These might include qualities of the player such as memory, spatial reasoning, patience, or even current fatigue level. For example, a puzzle game might consider a player's working memory (WM), such as their score in a test, to provide more intensive scaffolding or to inform its hint system. Similarly, an action adventure game with DDA capabilities could modify its difficulty curve based on its understanding of the player's temperament or tolerances (e.g., patience and persistence).

Beyond Input. SUKI may offer dynamic adaptation in the way a game processes and interprets input. Though of particular importance in the case of AVGs, this limits the potential scope of effect of the dynamic adaption to the portions of the game experience that address direct player interaction.

While the invention has been described with reference to the embodiments above, a person of ordinary skill in the art would understand that various changes or modifications may be made thereto without departing from the scope of the claims.

The invention claimed is:

1. A system that provides a gaming environment for a user, the system comprising:
 a user input sensor that tracks user motion and converts the user motion into body data, wherein the user input sensor is a motion-based sensor located remote from body of the user;
 a kinematic element module that receives the body data and organizes the body data into an organizational set of body data fields;
 a schema that receives the organizational set of body data fields and converts the organizational set of body data fields into input resolution data corresponding to the organizational set of body data fields; and
 an input resolution module that receives the input resolution data from the schema and creates a gaming command required to operate in the gaming environment;
 wherein the system includes sets of parameters corresponding to body capabilities, wherein the system automatically determines and defines user specific parameters during calibration to the user based on a user's movement constraints, and creates the gaming environment based on the user specific parameters, wherein the gaming environment encourages movement within the user specific parameters and discourages movement outside the user specific parameters, wherein the system detects changes in the user's movement constraints, and modifies the determined user specific parameters in real-time based on the detected changes, and wherein the system records the time at which the user specific parameters are modified.

2. The system of claim 1, wherein the organizational set of body data fields includes a node position corresponding to a user's body part in space.

3. The system of claim 2, wherein the organizational set of body data fields includes a vector corresponding to one node location to another node location.

4. The system of claim 3, wherein the organizational set of body data fields includes an angle between, corresponding to an angle formed between the vector and a second vector formed between one of the one node and the another node, and a third node.

5. The system of claim 1, wherein the organizational set of body data fields includes a node orientation corresponding to a directional orientation of a user's body part in space.

6. The system of claim 1, wherein the schema is implemented as a data string that can be loaded into the system by the user.

7. The system of claim 1, wherein the gaming command includes timing information.

8. The system of claim 1, wherein the gaming command includes state information.

9. The system of claim 1, wherein the organizational set of body data fields includes biometric data.

10. The system of claim 1, wherein the user specific parameters include a user motion and/or physical limitations, and wherein the gaming environment is provided with a structure within the user motion and/or physical limitations.

11. The system of claim 1, wherein the user specific parameters include a user body node extents and joint angle limitations that define user joints and angle limits, and wherein the gaming environment is provided with a structure within the user body node extents and the joint angle limitations.

12. The system of claim 1, wherein the user specific parameters include user body compound movement limitations that define user movements when multiple motions occur together, and wherein the gaming environment is provided with a structure within the user body compound movement limitations.

13. The system of claim 1, wherein the user specific parameters include a user body unavailable gestures limitations that define user movements that the user is incapable of, and wherein the gaming environment excludes unavailable gestures from the gaming environment.

14. The system of claim 1, wherein the system includes trigger parameters that are based at least on timing information, achievements of the user, and variable parameter interpolation.

15. A system for delivering physical therapy to a user, the system comprising:
 an active video gaming system comprising a motion detector capable of detecting physical motions of the user, wherein the motion detector is remote from the user, wherein the system includes setting parameters related to user capabilities, wherein the system automatically determines and defines user specific parameters during calibration to the user based on a user's movement constraints, and creates a gaming environment based on the user specific parameters, wherein the gaming environment encourages movement within the user specific parameters and discourages movement outside the user specific parameters, wherein the system detects changes in the user's movement constraints, and modifies the determined user specific parameters in real-time based on the detected changes, and wherein the system records the time at which the user specific parameters are modified.

16. The system of claim 15, wherein the user specific parameters may be set remotely from the active video gaming system.

17. The system of claim 15, wherein the system records user's movement as the user plays a game for later playback.

18. The system of claim 17, wherein the user's movement is reconstructed in a form of an avatar that masks a user's identity.

19. The system of claim 15, wherein the user capabilities including kinematic range of motion (ROM) limits are stored in a cloud and are available to the system to adapt gameplay based on the kinematic ROM limits.

* * * * *